(12) United States Patent
Andersen et al.

(10) Patent No.: US 7,771,996 B2
(45) Date of Patent: *Aug. 10, 2010

(54) FVII OR FVIIA VARIANTS

(75) Inventors: Kim Vilbour Andersen, Broenshoej (DK); Mads Röpke, Frederiksberg (DK); Jesper Mortensen Haaning, Birkeroed (DK); Steven Glazer, Copenhagen K (DK)

(73) Assignee: Bayer Healthcare LLC, Tarrytown, NY (US)

( * ) Notice: Subject to any disclaimer, the term of this patent is extended or adjusted under 35 U.S.C. 154(b) by 975 days.

This patent is subject to a terminal disclaimer.

(21) Appl. No.: 10/549,506

(22) PCT Filed: Mar. 22, 2004

(86) PCT No.: PCT/DK2004/000193

§ 371 (c)(1),
(2), (4) Date: Jul. 7, 2006

(87) PCT Pub. No.: WO2004/083361

PCT Pub. Date: Sep. 30, 2004

(65) Prior Publication Data

US 2007/0054366 A1 Mar. 8, 2007

Related U.S. Application Data

(60) Provisional application No. 60/456,547, filed on Mar. 20, 2003, provisional application No. 60/479,708, filed on Jun. 19, 2003.

(51) Int. Cl.
*C12Q 1/56* (2006.01)
*A61K 38/00* (2006.01)

(52) U.S. Cl. ............ 435/337; 435/13; 530/388.25; 530/389.3; 530/350; 514/2

(58) Field of Classification Search ............ None
See application file for complete search history.

(56) References Cited

U.S. PATENT DOCUMENTS

| | | | |
|---|---|---|---|
| 4,784,950 A | 11/1988 | Hagen et al. |
| 4,904,584 A | 2/1990 | Shaw |
| 5,041,376 A | 8/1991 | Gething et al. |
| 5,093,317 A | 3/1992 | Lewis et al. |
| 5,180,583 A | 1/1993 | Hedner |
| 5,225,537 A | 7/1993 | Foster |
| 5,258,288 A | 11/1993 | Wydro et al. |
| 5,288,629 A | 2/1994 | Berkner |
| 5,460,950 A | 10/1995 | Barr et al. |
| 5,504,064 A | 4/1996 | Morrisey et al. |
| 5,516,640 A | 5/1996 | Watanabe et al. |
| 5,580,560 A | 12/1996 | Nicolaisen et al. |
| 5,648,254 A | 7/1997 | Mulvihill et al. |
| 5,788,965 A | 8/1998 | Berkner et al. |
| 5,817,788 A | 10/1998 | Berkner et al. |
| 5,824,634 A | 10/1998 | Merchant |
| 5,824,639 A | 10/1998 | Berkner |
| 5,833,982 A | 11/1998 | Berkner et al. |
| 5,837,843 A | 11/1998 | Smirnov et al. |
| 5,847,085 A | 12/1998 | Esmon et al. |
| 5,861,374 A | 1/1999 | Berkner et al. |
| 5,891,843 A | 4/1999 | Turecek et al. |
| 5,965,425 A | 10/1999 | Barr et al. |
| 5,986,079 A | 11/1999 | Barr et al. |
| 6,013,620 A | 1/2000 | Turecek et al. |
| 6,017,882 A | 1/2000 | Nelsestuen |
| 6,100,061 A | 8/2000 | Reiter et al. |
| 6,132,730 A * | 10/2000 | Thorpe et al. ............ 424/198.1 |
| 6,423,826 B1 | 7/2002 | Nelsestuen |
| 6,475,725 B1 | 11/2002 | Reiter et al. |
| 6,693,075 B1 | 2/2004 | Nelsestuen |
| 6,747,003 B1 | 6/2004 | Nelsestuen |
| 6,762,286 B2 | 7/2004 | Nelsestuen |
| 6,806,063 B2 | 10/2004 | Pedersen et al. |
| 6,903,069 B2 | 6/2005 | Pingel et al. |
| 7,026,524 B2 | 4/2006 | Persson et al. |
| 7,220,837 B1 | 5/2007 | Nelsestuen |
| 2003/0100506 A1 | 5/2003 | Nelsestuen |
| 2003/0100740 A1 | 5/2003 | Persson et al. |
| 2003/0104978 A1 | 6/2003 | Persson et al. |
| 2003/0211094 A1 | 11/2003 | Nelsestuen |
| 2003/0211460 A1 | 11/2003 | Nelsestuen |
| 2005/0164932 A1 | 7/2005 | Haaning |
| 2006/0019336 A1 | 1/2006 | Pedersen et al. |

(Continued)

FOREIGN PATENT DOCUMENTS

EP 0 296 413 A2 12/1988

(Continued)

OTHER PUBLICATIONS

National heart lung and blood institute-diseases and condition index (2009, updated) what is hemophilia, www.nhlbi.nih.gov/health/dci/Diseases/hemophilia/hemophilia_what.html, pp. 1-2.*

(Continued)

*Primary Examiner*—Anand U Desai
*Assistant Examiner*—Samuel Liu

(57) ABSTRACT

Variants of FVII or FVIIa comprising at least one amino acid modification in position 196, 237 or 341 relative to hFVII or hFVIIa. The variants exhibit an increased clotting activity, i.e. reduced clotting time, compared to rhFVIIa.

18 Claims, 1 Drawing Sheet

U.S. PATENT DOCUMENTS

Figure 1:
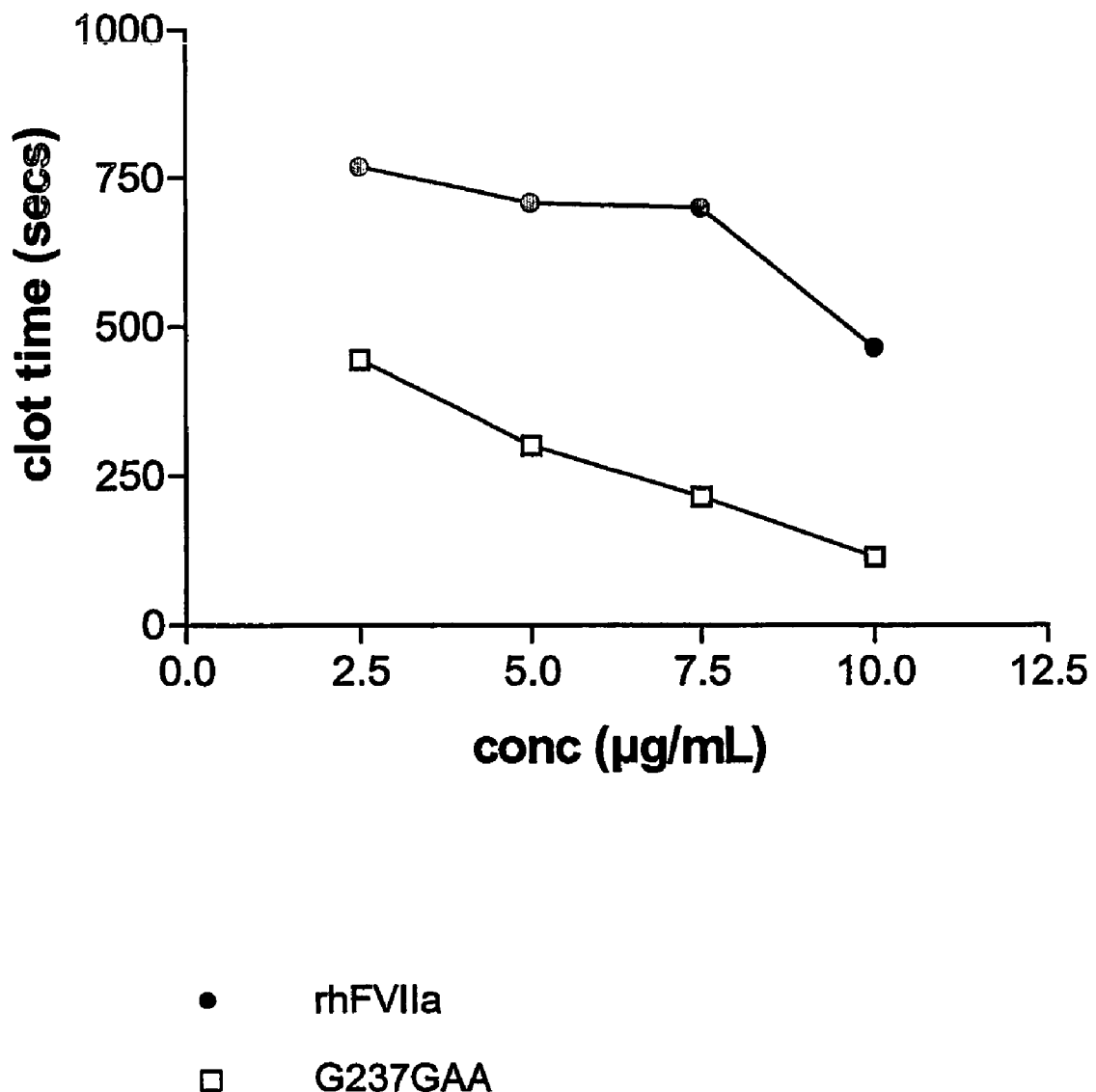

| | | |
|---|---|---|
| 2006/0111282 A1 | 5/2006 | Haaning |
| 2006/0166874 A1 | 7/2006 | Haaning |
| 2006/0228782 A1 | 10/2006 | Pedersen |
| 2006/0240524 A1 | 10/2006 | Pedersen |
| 2006/0240525 A1 | 10/2006 | Pedersen |
| 2006/0240526 A1 | 10/2006 | Haaning |
| 2006/0241041 A1 | 10/2006 | Haaning |
| 2006/0252127 A1 | 11/2006 | Pedersen |
| 2006/0252128 A1 | 11/2006 | Haaning |
| 2006/0252689 A1 | 11/2006 | Pedersen |
| 2006/0252690 A1 | 11/2006 | Pedersen |
| 2006/0258585 A1 | 11/2006 | Pedersen |
| 2006/0270000 A1 | 11/2006 | Haaning |
| 2006/0270001 A1 | 11/2006 | Haaning |
| 2006/0270002 A1 | 11/2006 | Haaning |
| 2006/0276377 A1 | 12/2006 | Haaning |
| 2007/0054366 A1 | 3/2007 | Andersen |
| 2007/0117756 A1 | 5/2007 | Haaning |
| 2007/0142280 A1 | 6/2007 | Pedersen |

FOREIGN PATENT DOCUMENTS

| | | |
|---|---|---|
| EP | 0 354 504 A2 | 2/1990 |
| EP | 0 370 205 A2 | 5/1990 |
| EP | 0 512 011 B1 | 11/1992 |
| WO | WO 88/10295 A1 | 12/1988 |
| WO | WO 91/11514 A1 | 8/1991 |
| WO | WO 92/15686 A1 | 9/1992 |
| WO | WO 94/27631 A1 | 12/1994 |
| WO | WO 96/00577 A1 | 1/1996 |
| WO | WO 98/32466 A1 | 7/1998 |
| WO | WO 98/35026 A1 | 8/1998 |
| WO | WO 99/03498 A1 | 1/1999 |
| WO | WO 99/03887 A1 | 1/1999 |
| WO | WO 99/20767 A1 | 4/1999 |
| WO | WO 99/66031 A2 | 12/1999 |
| WO | WO 00/26230 A1 | 5/2000 |
| WO | WO 00/26354 A1 | 5/2000 |
| WO | WO 00/28065 A1 | 5/2000 |
| WO | WO 00/54787 A1 | 9/2000 |
| WO | WO 00/66753 | 11/2000 |
| WO | WO 00/66753 A2 | 11/2000 |
| WO | WO 01/58935 A2 | 8/2001 |
| WO | WO 01/83725 A1 | 11/2001 |
| WO | WO 02/02764 | 1/2002 |
| WO | WO 02/03075 | 1/2002 |
| WO | WO 02/22776 A2 | 3/2002 |
| WO | WO 02/29025 | 4/2002 |
| WO | WO 02/38162 A1 | 5/2002 |
| WO | WO 02/077218 A1 | 10/2002 |
| WO | WO 03/027147 A2 | 4/2003 |
| WO | WO 03/037932 A2 | 5/2003 |
| WO | WO 03/055512 A1 | 7/2003 |
| WO | WO 03/093465 A1 | 11/2003 |
| WO | WO 2004/029091 A2 | 4/2004 |
| WO | WO 2004/083361 A2 | 9/2004 |

OTHER PUBLICATIONS

O'hara et al. (1987) Nucleotide sequence of the gene coding for human factor VII, a vitamin K-dependent protein participating in blood coagulation, Proc. Natl. Acad. Sci .U S A., vol. 84, No. 15, pp. 5158-5162.*

Hu et al. (2001) Targeting tissue factor on tumor vascular endothelial cells and tumor cells for immunotherapy in mouse models of prostatic cancer, Proc. Natl. Acad. Sci. U S A., vol. 98, No. 1, pp. 12180-12185.*

Persson, E., et al., "$Ca^{2+}$ Binding to the First Epidermal Growth Factor-like Domain of Factor VIIa Increases Amidolytic Activity and Tissue Factor Affinity," *J. Biological Chemistry* 272(32):19919-19924 (1997).

Petersen, L.C., et al., "Binding of $Zn^{2+}$ to a $Ca^{2+}$ loop allosterically attenuates the activity of factor VIIa and reduces its affinity for tissue factor," *Protein Science* 9:859-866 (2000).

Petrovan, R.J., et al., "Role of Residue $Phe^{225}$ in the Cofactor-Mediated, Allosteric Regulation of the Serine Protease Coagulation Factor VIIa," *Biochemistry* 39:14457-14463 (2000).

Petrovan, R.J., et al., "Residue Met(156) contributes to the labile enzyme conformation of coagulation factor VIIa" *J. Biol. Chem.* 276(9):6616-6620 (2001).

Ruf, W., et al., "Importance of Factor VIIa Gla-Domain Residue Arg-36 for Recognition of the Macromolecular Substrate Factor X Gla-Domain," *Biochemistry* 38:1957-1966 (1999).

Shah, A.M., et al., "Manipulation of the membrane binding site of vitamin K-dependent proteins: Enhanced biological function of human factor VII," *Proc. Natl. Acad. Sci. USA* 95:4229-4234 (1998).

Shobe, J., et al., "Macromolecular Substrate Affinity for the Tissue Factor-Factor VIIa Complex is Independent of Scissile Bond Docking," *J. Biological Chemistry* 274(34):24171-24175 (1999).

Shobe, J., et al., "Regulation of the Catalytic Function of Coagulation Factor VIIa by a Conformational Linkage of Surface Residue Glu 154 to the Active Site," *Biochemistry* 38:2745-2751 (1999).

Sorensen, B.B. et al., "Incorporation of an active site inhibitor in factor VIIa alters the affinity for tissue factor," *J. Biol. Chem.* 272(18):11863-11868 (1997).

Sridhara S. et al. "Activation of a recombinant human factor VII structural analogue alters its affinity of binding to tissue factor," *Am. J. Hematol.* 53(2):66-71 (1996).

Zhang, E. et al., "Structure of Extracellular Tissue Factor Complexed with Factor VIIa Inhibited with a BPTI Mutant," *J. Mol. Biol.* 285(5):2089-2104 (1999).

J. Toomey et al., Localization of the Human Tissue Factor Recognition Determinant of Human Factor VIIa, *J. Biol. Chem.* 266(29):19198-19202 (1991).

U.S. Appl. No. 11/279,541, Pedersen et al., Unpublished.

Pending claims of U.S. Appl. No. 10/031,005, Nelsestuen, Parent application published as 20296.

Seffernick et al., "Melamine Deaminase and Atrazine Chlorohydrolase: 98 Percent Identical but Functionally Different," J. Bacteriol. 183(8):2405-2410 (2001).

Seshadri et al., "Differences in the Metal Ion Structure between Sr- and Ca-Prothrombin Fragment 1," Biochemistry, 1994, 33:1087-1092.

Shen et al., "Enhancing the Activity of Protein C by Mutagenesis to Improve the Membrane-Binding Site: Studies Related to Proline 10," Biochemistry, 1997, 36(51):16025-16031.

Shen et al., "Enhancement of Human Protein C Function by Site-directed Mutagenesis of the γ-Carboxyglutamic Acid Domain," J. Biol. Chem., 1998, 273(47):31086-31091.

Smirnov at al., "A Chimeric Protein C Containing the Prothrombin Gla Domain Exhibits Increased Anticoagulant Activity and Altered Phospholipid Specificity,"J. Biol. Chem., 1998, 273(15):9031-9040.

Thariath et al., "Highly conserved residue arginine-15 is required for the $Ca^{2+}$-dependent properties of the γ-carboxyglutamic acid domain of human anticoagulation Protein C and activated Protein C," Biochem. J., 1997, 322:309-315.

Thim et al., "Amino Acid Sequence and Posttranslational Modification of Human Factor VIIa from Plasma and Transfected Baby Hamster Kidney Cells," Biochemistry, 1988, 27:7785-7793.

Thomsen et al., "Pharmacokinetics of recombinant factor VIIa in the rat—a comparison of bio-, immuno- and isotope assays," Thromb. Haemost., 1993, 70(3):458-464.

Vallette et al., "Construction of mutant and chimeric genes using the polymerase chain reaction," Nucleic Acids Res., 1989, 17(2):723-733.

Vrana et al., "Expression of tissue factor in tumor stroma correlates with progression to invasive human breast cancer: paracrine regulation by carcinoma cell-derived members of the transforming growth factor beta family," Cancer Res., 56:5063-5070 (1996).

Weber et al., "Modifications of Bovine Prothrombin Fragment 1 in the Presence and Absence of Ca(II) Ions," J. Biol. Chem., 1992, 267(7):4564-4569.

Wei et al., "Kinetic and Mechanistic Analysis of Prothrombin-Membrane Binding by Stopped-Flow Light Scattering," Biochemistry, 1982, 21:1949-1959.

Wells, "Additivity of Mutational Effects in Proteins," Biochem. 29(17):8509-8517 (1990).

Welsch et al., "Chemical Modification of Prothrombin Fragment 1: Documentation of Sequential, Two-Stage Loss of Protein Function," Biochemistry, 1988, 27:4933-4938.

Welsch and Nelsestuen, "Amino-terminal alanine functions in a calcium-specific process essential for membrane binding by prothrombin fragment 1," Biochemistry, 1988, 27:4939-4945.

Yan et al., "Characterization and Novel Purification of Recombinant Human Protein C from Three Mammalian Cell Lines," Bio/Technology, 1990, 8:655-661.

Zhang et al., "Role of Individual γ-Caboxyglutamic Acid Residues of Activated Human Protein C in Defining its In Vitro Anticoagulant Activity," Blood, 1992, 80(4):942-952.

Zwaal et al., "Lipid-protein interactions in blood coagulation," Biochimica et Biophysica Acta, 1998, 1376:433-453.

Arnlijots et al., "Prevention of experimental arterial thrombosis by topical administration of active site-inactivated inactivated factor VIIa," J. Vasc. Surg., 1997, 25(2):341-346.

Bauer, "Treatment of factor VII deficiency with recombinant factor VIIa," Haemostasis, 1996, 26 (Suppl. 1):155-158.

Broze et al., "Monoclonal anti-human factor VII antibodies. Detection in plasma of a second protein antigenically and genetically related to factor VII," J. Clin. Invest., 1985, 76:937-946.

Choudhri et al., "Targeted Inhibition of Intrinsic Coagulation Limits Cerebral Injury in Stroke without Increasing Intracerebral Hemorrhage," J. Exp. Med., 1999, 190:91-99.

Christiansen et al., "Hydrophobic Amino Acid Residues of Human Anticoagulation Protein C that Contribute to its Functional Binding to Phospholipid Vesicles," Biochemistry, 1995, 34:10376-10382.

Dackiw et al., "Prevention of endotoxin-induced mortality by antitissue factor immunization," Arch. Surg., 1996, 131:1273-1278.

Dahlback, "Inherited Thrombophilia: Resistance to Activated Protein C as a Pathogenic Factor of Venous Thromboemolism," Blood, 1995, 85:607-614.

Database EMBL, "Coagulation factor VII (EC 3.4.21.21)(Serum prothrombin conversion accelerator)," "Bovine Factor VII. Its purification and complete amino acid sequence," ID FA7_BOVIN, Aug. 1, 1991 (3 pages).

"Docking of Tissue Factor and Factor VIIa Initiates Blood Coagulation," at http://www.sdsc.edu.IOTW/week46.96/ (1996).

Esmon et al., "Isolation of a membrane-bound cofactor for thrombin-catalyzed activation of protein C," J. Biol. Chem., 1982, 257:859-864.

Evans, Jr. and Nelsestuen, "Importance of cis-Proline 22 in the Membrane-Binding Conformation of Bovine Prothrombin," Biochemistry, 1996, 35:8210-8215.

Evans and Nelsestuen, "Importance of Cis-Proline 22 and the Aromatic Stack (Residues 41-45) for Prothrombin-Membrane Binding," Protein Sci., 1996, 5(Suppl. 1):163, Abstract #606-S.

Felgner et al., "Lipofection: a highly efficient, lipid-mediated DNA-transfection procedure," Proc. Natl. Acad. Sci. USA, 1987, 84:7413-7417.

Fiore et al., "The biochemical basis for the apparent defect of soluble mutant tissue factor in enhancing the proteolytic activities of factor VIIa," J. Biol. Chem., 1994, 269:143-149.

Freedman et al., "Identification of the phospholipid binding site in the vitamin K-dependent blood coagulation protein factor IX," J. Biol. Chem., 1996, 271(27):16227-16236.

Furie and Furie, "The molecular basis of blood coagulation," Cell, 1988, 53:506-518.

Guo et al., "Protein Tolerance to random amino acid change," Proc. Natl. Acad. Sci. 101(25):9205-9210 (2004).

Han et al., "Isolation of a protein Z-dependent plasma protease inhibitor," Proc. Natl. Acad. Sci. USA, 1998, 95:9250-9255.

He et al., "Expression and functional characterization of chimeras between human and bovine vitamin-K-dependent protein-S-defining modules important for the species specificity of the activated protein C cofactor activity," Eur. J. Biochem., 1995, 227:433-440.

Hedner et al., "Recombinant Activated Factor VII in the Treatment of Bleeding Episodes in Patients with Inherited and Acquired Bleeding Disorders," Transfus. Med. Rev., 1993, 7:78-83.

Hope et al., "Production of Large Unilamellar Vesicles by a Rapid Extrusion Procedure. Characterization of Size Distribution, Trapped Volume and Ability to Maintain a Membrane Potential," Biochem. Biophys. Acta, 1985, 812:55-65.

Hoskins et al., "Cloning and characterization of human liver cDNA encoding a protein S precursor," Proc. Natl. Acad. Sci. USA, 1987, 84:349-353.

Huang, , "Studies on Phosphatidylcholine Vesicles. Formation and Physical Characteristics," Biochemisty, Biochemistry, 1969, 8:344-352.

Humphries et al., "Chemical methods of protein synthesis and modification," Curr. Opin. Biotechnol., 1991, 2(4):539-543.

Jurlander et al., "Recombinant Activated Factor VII (rFVIIa): Characterization, Manufacturing, and Clinical Development," Semin. Thromb. Hemos., 2001, 27(4):373-383.

Leff, "Genetically Stripped-Down Factor VIII Corrects Bleeding Disorder in Hemophiliac Mice," BioWorld Today, 1997, 8(209):1,6.

Lu and Nelsestuen, "Dynamic Features of Prothrombin Interaction with Phospholipid Vesicles of Different Size and Composition: Implications for Protein—Membrane Contact," Biochemistry, 1996, 35:8193-8200.

Lu and Nelsestuen, "The prothrombinase reaction: "mechanism switching" between Michaelis-Menten and non-Michaelis-Menten behaviors," Biochemistry, 1996, 35:8201-8209.

Martinez et al., "Underdecarboxlyation of Vitamin K-Dependent Proteins: Occasionally Severe, Possibly Universal," Proceedings of the 49th ASMS Conference on Mass Spectrometry and Allied Topics, May 27-31, 2001, Chicago, Illinois, 2 pgs.

Matsubara et al., "A receptor tyrosine kinase, Sky, and its ligand Gas 6 are expressed in gonads and support primordial germ cell growth or survival in culture," Dev. Biol., 1996, 180:499-510.

Mayer et al., "Prothrombin Association with Phospholipid Monolayers," Biochemistry, 1983, 22(2):316-321.

Mayer, "Ultra-early hemostatic therapy for intracerebral hemorrhage," Stroke 2003, 34:224-229.

McDonald et al., "Comparison of Naturally Occurring Vitamin K-dependent Proteins: Correlation of Amino Acid Sequences and Membrane Binding Properties Suggests a Membrane Contact Site," Biochemistry, 1997, 36:5120-5127.

McDonald et al., "Ionic Properties of Membrane Association by Vitamin K-Dependent Proteins: The Case for Univalency," Biochemistry, 1997, 36(50):15589-15598.

Morrissey et al., "Quantitation of Activated Factor VII Levels in Plasma Using a Tissue Factor Mutant Selectively Deficient in Promoting Factor VII Activation," Blood, 1993, 81(3):734-744.

Muir et al., "The chemical synthesis of proteins," Curr. Opin. Biotechnol., 1993, 4(4):420-427.

Nakagaki et al., "Initiation of the Extrinsic Pathway of Blood Coagulation: Evidence for the Tissue Factor Dependent Autoactivation of Human Coagulation Factor VII," Biochemistry, 1991, 30:10819-10824.

Nelsestuen et al., "Membrane association with multiple calcium ions: vitamin-K-dependent proteins, annexins and pentraxins," Current Opinion in Structural Biology 9:433-437 (1999).

Nelsestuen, "Enhancement of Vitamin-K-Dependent Protein Function by Modification of the gamma-Carboxyglutamic Acid Domain: Studies of Protein C and Factor VII," Trends Cardiovasc. Med. 9(6):162-167 (1999).

Nelsestuen et al., "Vitamin K-Dependent Proteins," in 58 Vitamins and Hormones: Advances in Research and Applications (Gerald Litwack ed., Academic Press, 2000), pp. 355-389.

Nelsestuen et al., "Equilibria Involved in Prothrombin- and Blood Clotting Factor X-Membrane Binding," Biochemistry, 1977, 16(19):4164-4171.

Nelsestuen and Suttie, "Properties of Asialo and Aglycoprothrombin," Biochem. Biophys. Res. Commun., 1971, 45:198-203.

Nicolaes et al., "A prothrombinase-based assay for detection of resistance to activated protein C," Thromb. Haemost., 1996, 76:404-410.

Nicolaisen et al., "Immunological aspects of recombinant factor VIIa (rFVIIa) in clinical use," Thromb. Haemost., 1996, 76:200-204.

Okafuji et al., EMBL Data Library, Accession No. S18994, Sep. 10, 1999 (protein C activated precursor, sequence) (Score Search).

Perera et al., "Trans-cis Isomerization of Proline 22 in Bovine Prothrombin Fragment 1: A Surprising Result of Structural Characterization," Biochemistry, 1998, 37:10920-10927.

Petersen et al., "Quenching of the amidolytic activity of one-chain tissue-type plasminogen activator by mutation of lysine-416," Biochemistry, 1990, 29:3451-3457.

Petrovan et al., "Residue Met$^{156}$ contributes to the labile enzyme conformation of coagulation factor VIIa," J. Biol. Chem. 2001, 276(9):6616-6620.

Ratcliffe et al., "The importance of Specific γ-Carboxyglutamic Acid Residues in Prothrombin," J. Biol. Chem., 1993, 268(32):24339-24345.

Resnick and Nelsestuen, "Prothrombin-Membrane Interaction. Effects of Ionic Strength, pH, and Temperature," Biochemistry, 1980, 19(13):3028-3033.

Rezaie and Esmon, "The function of calcium in protein C activation by thrombin and the thrombin-thrombomodulin complex can be distinguished by mutational analysis of protein C derivatives," J. Biol. Chem., 1992, 267:26104-26109.

Sakai et al., "The γ-Carboxyglutamic Acid Domain of Human Factor VIIA is Essential for Its Interaction with Cell Surface Tissue Factor," J. Biol. Chem., 1990, 265(4):1890-1894.

Schmidel et al., "Organization of the Human Protein S Genes," J. Biol. Chem., 1990, 29(34):7845-7852.

Schulman et al., "Feasibility of using recombinant factor VIIa in continuous infusion," Thromb. Haemost., 1996, 75(3):432-436.

Schwalbe et al., "Protein Structural Requirements and Properties of Membrane Binding by γ-Carboxyglutamic Acid-containing Plasma Proteins and Peptides," J. Biol. Chem., 1989, 264:20288-.

Harvey, Stephen B., et al., "Mutagenesis of the γ-carboxyglutamic acid domain of human factor VII to generate maximum enhancement of the membrane contact site," The Journal of Biological Chemistry 278(10):8363-8369 (Mar. 2003).

Henderson, Nicole et al., "Response of factor VII and IX-deficient blood to wild type and high membrane affinity mutant factor VIIa in an in vitro whole blood clotting assay: possible correlation to clinical outcome," Thromb Haemost 88:98-103 (2002).

Stone, Matthew et al., "Unusual benefits of macromolecular shielding by polyethylene glycol for reactions at the diffusional limit: the case of factor VIIai and tissue factor," Biochemistry 41:15820-15825 (2002).

Zhang, Li et al., "The contributions of individual γ-carboxyglutamic acid residues in the calcium-dependent binding of recombinant human protein c to acidic phospholipid vesicles," The Journal of Biological Chemistry 268 (16):12040-12045 (Jun. 1993).

Bharadwaj, D., et al., "Factor VII Central—A Novel Mutation in the Catalytic Domain that Reduces Tissue Factor Binding, Impairs Activation by Factor XA, and Abolishes Amidolytic and Coagulant Activity," J. Biological Chemistry 271(48):30685-30691 (1996).

Bjoern, S., et al., "Human Plasma and Recombinant Factor VII—Characterization of O-Glycosylations at Serine Residues 52 and 60 and Effects of Site-Directed Mutagenesis of Serine 52 to Alanine," J. Biological Chemistry 266(17):11051-11057 (1991).

Chang, J-Y., et al., "Replacing the First Epidermal Growth Factor-like Domain of Factor IX with That of Factor VII Enhances Activity In Vitro and in Canine Hemophilia B," J. Clin. Invest. 100(4):886-892 (1997).

Chang, Y-J., et al., "Engineered Recombinant Factor VII Q$^{217}$ Variants with Altered Inhibitor Specificities," Biochemistry 38:10940-10948 (1999).

Cheung, W.F. et al., "Localization of an Epitope of Calcium-Dependent Monoclonal Antibody to the N-Terminal Region of the Gla Domain of Human Factor VII", Thrombosis Research, 79(2):199-206 (1995).

Cheung, W.F. et al., "Localization of a metal-dependent epitope to the amino terminal residues 33-40 of human factor IX", Thrombosis Research, 80(5):419-427 (1995).

Database EMBL, "Gallus gallus anticoagulant protein C precursor (PROC) mRNA, complete cds", Database Accession No. AF465270, Feb. 2, 2003.

Database UNIPROT, "Coagulation factor VII (EC 3.4.21.21) (Serum prothrombin conversion accelerator)", Database Accession No. P22457, Aug. 1, 1991.

Dickinson, C.D., et al., "Identification of surface residues mediating tissue factor binding and catalytic function of the serine protease factor VIIa," Proc. Natl. Acad. Sci. USA 93:14379-14384 (1996).

Dickinson, C.D., et al., "Active Site Modification of Factor VIIa Affects Interactions of the Protease Domain with Tissue Factor," J. Biological Chemistry 272(32):19875-19879 (1997).

Dickinson, C. D. et al., "Influence of Cofactor Binding and Active Site Occupancy on the Conformation of the Macromolecular Substrate Exosite of Factor VIIa", J. Mol. Biol. 277:959-971 (1998).

Hedner, U. "NovoSeven as a universal haemostatic agent." Blood Coagul. Fibrinolysis 11 Suppl 1:S107-S111 (2000).

Higashi, S. et al. "Molecular mechanism of tissue factor-mediated acceleration of factor VIIa activity," J. Biol. Chem. 271(43):26569-74 (1996).

Huang, Q., et al., "Substrate Recognition by Tissue Factor-Factor VIIa—Evidence for Interaction of Residues Lys $^{165}$ and Lys $^{166}$ of Tissue Factor with the 4-Carboxyglutamate-Rich Domain of Factor X," J. Biological Chemistry 271(36):21752-21757 (1996).

Iino, M., et al., "Functional Consequences of Mutations in Ser-52 and Ser-60 in Human Blood Coagulation Factor VII," Archives Biochem. Biophys. 352(2):182-192 (1998).

Iakhiaev, A. et al. "The role of catalytic cleft and exosite residues of factor VIIa for complex formation with tissue factor pathway inhibitor", Thromb. Haemost. 85(3):458-463 (2001).

Jin, J., et al., "Factor VIIa's First Epidermal Growth Factor-like Domain's Role in Catalytic Activity," Biochemistry 38:1185-1192 (1999).

Jin, J. et al., "Four Loops of the Catalytic Domain of Factor VIIa Mediate the Effect of the First EGF-like Domain Substitution on Factor VIIa Catalytic Activity", J. Mol. Biol. 307:1503-1517 (2001).

Kelly, C.R., et al., "Ca$^{2+}$ Binding to the First Epidermal Growth Factor Module of Coagulation Factor VIIa Is Important for Cofactor Interaction and Proteolytic Function," J. Biological Chemistry 272(28):17467-17472 (1997).

Kemball-Cook, G., et al., "Coagulation Factor VII Gln$^{100}$Arg—Amino Acid Substitution at the Epidermal Growth Factor 2-Protease Domain Interface Results in Severely Reduced Tissue Factor Binding and Procoagulant Function," J. Biological Chemistry 273(14):8516-8521 (1998).

Leonard, B.J.N., et al., "Activation and Active Site Occupation Alter Conformation in the Region of the First Epidermal Growth Factor-like Domain of Human Factor VII," J. Biological Chemistry 275(45):34894-34900 (2000).

Mayer, S.A. "Ultra-early hemostatic therapy for intracerebral hemorrhage," Stroke 34(1):224-229 (2003).

Nelsestuen, G.L. et al. "Elevated function of blood clotting factor VIIa mutants that have enhanced affinity for membranes. Behavior in a diffusion-limited reaction," J. Biol. Chem. 276(43):39825-39831 (2001).

Neuenschwander, P.F. et al., "Alteration of the Substrate and Inhibitor Specificities of Blood Coagulation Factor VIIa: Importance of Amino Acid Residue K192", Biochemistry 34:8701-8707 (1995).

Persson, E., et al., "Site-directed mutagenesis but not γ-carboxylation of Glu-35 in factor VIIa affects the association with tissue factor," FEBS Letters 385:241-243 (1996).

Persson, E., "Characterization of the interaction between the light chain of factor VIIa and tissue factor," FEBS Letters 413:359-363 (1997).

* cited by examiner

```
                      SEQUENCE LISTING

<160> NUMBER OF SEQ ID NOS: 21

<210> SEQ ID NO 1
<211> LENGTH: 1338
<212> TYPE: DNA
<213> ORGANISM: Homo sapiens
<220> FEATURE:
<221> NAME/KEY: CDS
<222> LOCATION: (115)..(1338)

<400> SEQUENCE: 1
atggtcagcc aggccctccg cctcctgtgc ctgctcctgg ggctgcaggg ctgcctggct     60
gccgtcttcg tcacccagga ggaagcccat ggcgtcctgc atcgccggcg ccgg gcc     117
                                                              Ala
                                                              1 aat gcc ttt ctg gaa gag ctc cgc cct ggc tcc ctg gaa cgc gaa tgc     165
Asn Ala Phe Leu Glu Glu Leu Arg Pro Gly Ser Leu Glu Arg Glu Cys
        5                  10                  15 aaa gag gaa cag tgc agc ttt gag gaa gcc cgg gag att ttc aaa gac     213
Lys Glu Glu Gln Cys Ser Phe Glu Glu Ala Arg Glu Ile Phe Lys Asp
            20                  25                  30 gct gag cgg acc aaa ctg ttt tgg att agc tat agc gat ggc gat cag     261
Ala Glu Arg Thr Lys Leu Phe Trp Ile Ser Tyr Ser Asp Gly Asp Gln
        35                  40                  45 tgc gcc tcc agc cct tgc cag aac ggg ggc tcc tgc aaa gac cag ctg     309
Cys Ala Ser Ser Pro Cys Gln Asn Gly Gly Ser Cys Lys Asp Gln Leu
50                  55                  60                  65 cag agc tat atc tgc ttc tgc ctg cct gcc ttt gag ggg cgc aat tgc     357
Gln Ser Tyr Ile Cys Phe Cys Leu Pro Ala Phe Glu Gly Arg Asn Cys
                70                  75                  80 gaa acc cat aag gat gac cag ctg att tgc gtc aac gaa aac ggg ggc     405
Glu Thr His Lys Asp Asp Gln Leu Ile Cys Val Asn Glu Asn Gly Gly
            85                  90                  95 tgc gag cag tac tgc agc gat cac acg ggc acg aag cgc agc tgc cgc     453
Cys Glu Gln Tyr Cys Ser Asp His Thr Gly Thr Lys Arg Ser Cys Arg
        100                 105                 110 tgc cac gaa ggc tat agc ctc ctg gct gac ggg gtg tcc tgc acg ccc     501
Cys His Glu Gly Tyr Ser Leu Leu Ala Asp Gly Val Ser Cys Thr Pro
    115                 120                 125 acg gtg gaa tac cct tgc ggg aag att ccc att cta gaa aag cgg aac     549
Thr Val Glu Tyr Pro Cys Gly Lys Ile Pro Ile Leu Glu Lys Arg Asn
130                 135                 140                 145 gct agc aaa ccc cag ggc cgg atc gtc ggc ggg aag gtc tgc cct aag     597
Ala Ser Lys Pro Gln Gly Arg Ile Val Gly Gly Lys Val Cys Pro Lys
                150                 155                 160
```

```
ggg gag tgc ccc tgg cag gtc ctg ctc ctg gtc aac ggg gcc cag ctg      645
Gly Glu Cys Pro Trp Gln Val Leu Leu Leu Val Asn Gly Ala Gln Leu
            165                 170                 175 tgc ggc ggg acc ctc atc aat acc att tgg gtc gtg tcc gcc gct cac      693
Cys Gly Gly Thr Leu Ile Asn Thr Ile Trp Val Val Ser Ala Ala His
        180                 185                 190 tgc ttc gat aag att aag aat tgg cgg aac ctc atc gct gtg ctc ggc      741
Cys Phe Asp Lys Ile Lys Asn Trp Arg Asn Leu Ile Ala Val Leu Gly
    195                 200                 205 gaa cac gat ctg tcc gag cat gac ggg gac gaa cag tcc cgc cgg gtg      789
Glu His Asp Leu Ser Glu His Asp Gly Asp Glu Gln Ser Arg Arg Val
210                 215                 220                 225 gct cag gtc atc att ccc tcc acc tat gtg cct ggc acg acc aat cac      837
Ala Gln Val Ile Ile Pro Ser Thr Tyr Val Pro Gly Thr Thr Asn His
                230                 235                 240 gat atc gct ctg ctc cgc ctc cac cag ccc gtc gtg ctc acc gat cac      885
Asp Ile Ala Leu Leu Arg Leu His Gln Pro Val Val Leu Thr Asp His
            245                 250                 255 gtc gtg cct ctg tgc ctg cct gag cgg acc ttt agc gaa cgc acg ctg      933
Val Val Pro Leu Cys Leu Pro Glu Arg Thr Phe Ser Glu Arg Thr Leu
        260                 265                 270 gct ttc gtc cgc ttt agc ctc gtg tcc ggc tgg ggc cag ctg ctc gac      981
Ala Phe Val Arg Phe Ser Leu Val Ser Gly Trp Gly Gln Leu Leu Asp
    275                 280                 285 cgg ggc gct acc gct ctc gag ctg atg gtg ctc aac gtc ccc cgg ctg     1029
Arg Gly Ala Thr Ala Leu Glu Leu Met Val Leu Asn Val Pro Arg Leu
290                 295                 300                 305 atg acc cag gac tgc ctg cag cag tcc cgc aaa gtg ggg gac tcc ccc     1077
Met Thr Gln Asp Cys Leu Gln Gln Ser Arg Lys Val Gly Asp Ser Pro
                310                 315                 320 aat atc acg gag tat atg ttt tgc gct ggc tat agc gat ggc tcc aag     1125
Asn Ile Thr Glu Tyr Met Phe Cys Ala Gly Tyr Ser Asp Gly Ser Lys
            325                 330                 335 gat agc tgc aag ggg gac tcc ggc ggg ccc cat gcc acg cac tat cgc     1173
Asp Ser Cys Lys Gly Asp Ser Gly Gly Pro His Ala Thr His Tyr Arg
        340                 345                 350 ggg acc tgg tac ctc acc ggg atc gtc agc tgg ggc cag ggc tgc gcc     1221
Gly Thr Trp Tyr Leu Thr Gly Ile Val Ser Trp Gly Gln Gly Cys Ala
    355                 360                 365 acg gtg ggg cac ttt ggc gtc tac acg cgc gtc agc cag tac att gag     1269
Thr Val Gly His Phe Gly Val Tyr Thr Arg Val Ser Gln Tyr Ile Glu
370                 375                 380                 385 tgg ctg cag aag ctc atg cgg agc gaa ccc cgg ccc ggg gtg ctc ctg     1317
Trp Leu Gln Lys Leu Met Arg Ser Glu Pro Arg Pro Gly Val Leu Leu
                390                 395                 400 cgg gcc cct ttc cct tga taa                                         1338
Arg Ala Pro Phe Pro
            405

<210> SEQ ID NO 2
<211> LENGTH: 406
<212> TYPE: PRT
<213> ORGANISM: Homo sapiens

<400> SEQUENCE: 2

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30
```

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 3
<211> LENGTH: 1357
<212> TYPE: DNA
<213> ORGANISM: Artificial
<220> FEATURE:
<223> OTHER INFORMATION: Synthetic gene for optimized expression of hFVII

<400> SEQUENCE: 3

```
ggatcccgcc accatggtca gccaggccct ccgcctcctg tgcctgctcc tggggctgca      60
gggctgcctg gctgccgtct tcgtcaccca ggaggaagcc catggcgtcc tgcatcgccg     120
gcgccgggcc aatgcctttc tggaagagct ccgccctggc tccctggaac gcgaatgcaa     180
agaggaacag tgcagctttg aggaagcccg ggagattttc aaagacgctg agcggaccaa     240
actgttttgg attagctata gcgatggcga tcagtgcgcc tccagccctt gccagaacgg     300
gggctcctgc aaagaccagc tgcagagcta tatctgcttc tgcctgcctg cctttgaggg     360
gcgcaattgc gaaacccata aggatgacca gctgatttgc gtcaacgaaa acggggctg     420
cgagcagtac tgcagcgatc acacgggcac gaagcggagc tgccgctgcc acgaaggcta     480
tagcctcctg gctgacgggg tgtcctgcac gcccacggtg aataccctt gcgggaagat     540
tcccattcta gaaaagcgga acgctagcaa accccagggc cggatcgtcg gcgggaaggt     600
ctgccctaag ggggagtgcc cctggcaggt cctgctcctg gtcaacgggg cccagctgtg     660
cggcgggacc ctcatcaata ccatttgggt cgtgtccgcc gctcactgct tcgataagat     720
taagaattgg cggaacctca tcgctgtgct cggcgaacac gatctgtccg agcatgacgg     780
ggacgaacag tcccgccggg tggctcaggt catcattccc tccacctatg tgcctggcac     840
gaccaatcac gatatcgctc tgctccgcct ccaccagccc gtcgtgctca ccgatcacgt     900
cgtgcctctg tgcctgcctg agcggacctt tagcgaacgc acgctggctt tcgtccgctt     960
tagcctcgtg tccggctggg gccagctgct cgaccggggc gctaccgctc tcgagctgat    1020
ggtgctcaac gtccccggc tgatgaccca ggactgcctg cagcagtccc gcaaagtggg    1080
ggactccccc aatatcacgg agtatatgtt ttgcgctggc tatagcgatg gctccaagga    1140
tagctgcaag ggggactccg gcgggcccca tgccacgcac tatcgcggga cctggtacct    1200
caccgggatc gtcagctggg gccagggctg cgccacggtg gggcactttg gcgtctacac    1260
gcgcgtcagc cagtacattg agtggctgca aagctcatg cggagcgaac cccggcccgg    1320
ggtgctcctg cgggccccctt tcccttgata aagctt                              1357
```

<210> SEQ ID NO 4
<211> LENGTH: 31
<212> TYPE: DNA
<213> ORGANISM: Artificial
<220> FEATURE:
<223> OTHER INFORMATION: Primer

<400> SEQUENCE: 4

```
agctggctag ccactgggca ggtaagtatc a                                      31
```

<210> SEQ ID NO 5
<211> LENGTH: 31
<212> TYPE: DNA
<213> ORGANISM: Artificial
<220> FEATURE:
<223> OTHER INFORMATION: Primer

<400> SEQUENCE: 5

```
tggcgggatc cttaagagct gtaattgaac t                                      31
```

<210> SEQ ID NO 6
<211> LENGTH: 38
<212> TYPE: DNA
<213> ORGANISM: Artificial

```
<220> FEATURE:
<223> OTHER INFORMATION: Primer

<400> SEQUENCE: 6
cccattctag aaaagcggaa cgccagcaaa ccccaggg                          38

<210> SEQ ID NO 7
<211> LENGTH: 34
<212> TYPE: DNA
<213> ORGANISM: Artificial
<220> FEATURE:
<223> OTHER INFORMATION: Primer

<400> SEQUENCE: 7
ccaattctta atcttgttga agcagtgagc ggcg                              34

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
ctccgtgata ttgggggagt c                                            21

<210> SEQ ID NO 9
<211> LENGTH: 34
<212> TYPE: DNA
<213> ORGANISM: Artificial
<220> FEATURE:
<223> OTHER INFORMATION: Primer

<400> SEQUENCE: 9
cgccgctcac tgcttcaaca agattaagaa ttgg                              34

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
cgctctcgag ctgatggtgc tc                                           22

<210> SEQ ID NO 11
<211> LENGTH: 22
<212> TYPE: DNA
<213> ORGANISM: Artificial
<220> FEATURE:
<223> OTHER INFORMATION: Primer

<400> SEQUENCE: 11
caaacaacag atggctggca ac                                           22

<210> SEQ ID NO 12
<211> LENGTH: 34
<212> TYPE: DNA
<213> ORGANISM: Artificial
<220> FEATURE:
<223> OTHER INFORMATION: Primer

<400> SEQUENCE: 12
cgccgctcac tgcttcaaga agattaagaa ttgg                              34
```

-continued

<210> SEQ ID NO 13
<211> LENGTH: 34
<212> TYPE: DNA
<213> ORGANISM: Artificial
<220> FEATURE:
<223> OTHER INFORMATION: Primer

<400> SEQUENCE: 13
ccaattctta atcttcttga agcagtgagc ggcg                                34

<210> SEQ ID NO 14
<211> LENGTH: 33
<212> TYPE: DNA
<213> ORGANISM: Artificial
<220> FEATURE:
<223> OTHER INFORMATION: Primer

<400> SEQUENCE: 14
ctccacctat gtgcctctga cgaccaatca cga                                 33

<210> SEQ ID NO 15
<211> LENGTH: 33
<212> TYPE: DNA
<213> ORGANISM: Artificial
<220> FEATURE:
<223> OTHER INFORMATION: Primer

<400> SEQUENCE: 15
tcgtgattgg tcgtcagagg cacataggtg gag                                 33

<210> SEQ ID NO 16
<211> LENGTH: 29
<212> TYPE: DNA
<213> ORGANISM: Artificial
<220> FEATURE:
<223> OTHER INFORMATION: Primer

<400> SEQUENCE: 16
ccaaggatgc caggggact ccggcgggc                                       29

<210> SEQ ID NO 17
<211> LENGTH: 33
<212> TYPE: DNA
<213> ORGANISM: Artificial
<220> FEATURE:
<223> OTHER INFORMATION: Primer

<400> SEQUENCE: 17
gcccgccgga gtccccctgg cagctatcct tgg                                 33

<210> SEQ ID NO 18
<211> LENGTH: 36
<212> TYPE: DNA
<213> ORGANISM: Artificial
<220> FEATURE:
<223> OTHER INFORMATION: Primer

<400> SEQUENCE: 18
acctatgtgc ctggcgctgc cacgaccaat cacgat                              36

<210> SEQ ID NO 19
<211> LENGTH: 36
<212> TYPE: DNA
<213> ORGANISM: Artificial
<220> FEATURE:
<223> OTHER INFORMATION: Primer

```
<400> SEQUENCE: 19
atcgtgattg gtcgtggcag cgccaggcac ataggt                              36

<210> SEQ ID NO 20
<211> LENGTH: 4
<212> TYPE: PRT
<213> ORGANISM: Artificial
<220> FEATURE:
<223> OTHER INFORMATION: Position 237 Inserted Sequence

<400> SEQUENCE: 20

Gly Ala Ala Ala
1

<210> SEQ ID NO 21
<211> LENGTH: 5
<212> TYPE: PRT
<213> ORGANISM: Artificial
<220> FEATURE:
<223> OTHER INFORMATION: Position 237 Inserted Sequence

<400> SEQUENCE: 21

Gly Ala Ala Ala Ala
1               5
```

FVII OR FVIIA VARIANTS

FIELD OF THE INVENTION

The present invention relates to novel FVII or FVIIa variants comprising at least one amino acid modification in a position selected from the group consisting of 196, 237 and 341. The present invention also relates to use of such polypeptide variants in therapy, in particular for the treatment of a variety of coagulation-related disorders.

BACKGROUND OF THE INVENTION

Blood coagulation is a process consisting of a complex interaction of various blood components (or factors) that eventually results in a fibrin clot. Generally, the blood components participating in what is referred to as the "coagulation cascade" are proenzymes or zymogens, i.e. enzymatically inactive proteins that are converted into an active form by the action of an activator. One of these coagulation factors is factor VII (FVII).

FVII is a vitamin K-dependent plasma protein synthesized in the liver and secreted into the blood as a single-chain glycoprotein with a molecular weight of 53 kDa (Broze & Majerus, *J. Biol. Chem.* 1980; 255:1242-1247). The FVII zymogen is converted into an activated form (FVIIa) by proteolytic cleavage at a single site, R152-I153, resulting in two chains linked by a single disulfide bridge. FVIIa in complex with tissue factor (TF), the FVIIa complex, is able to convert both FIX and FX into their activated forms, followed by reactions leading to rapid thrombin production and fibrin formation (Østerud & Rapaport, *Proc Natl Acad Sci USA* 1977; 74:5260-5264).

FVII undergoes post-translational modifications, including vitamin K-dependent carboxylation resulting in ten γ-carboxyglutamic acid residues in the N-terminal region of the molecule. Thus, residues number 6, 7, 14, 16, 19, 20, 25, 26, 29 and 35 shown in SEQ ID NO:2 are γ-carboxyglutamic acids residues in the Gla domain important for FVII activity. Other post-translational modifications include sugar moiety attachment at two naturally occurring N-glycosylation sites at positions 145 and 322, respectively, and at two naturally occurring O-glycosylation sites at positions 52 and 60, respectively.

The gene coding for human FVII (hFVII) has been mapped to chromosome 13 at q34-qter 9 (de Grouchy et al., *Hum Genet* 1984; 66:230-233). It contains nine exons and spans 12.8 Kb (O'Hara et al., *Proc Natl Acad Sci USA* 1987; 84:5158-5162). The gene organisation and protein structure of FVII are similar to those of other vitamin K-dependent procoagulant proteins, with exons 1a and 1b encoding for signal sequence; exon 2 the propeptide and Gla domain; exon 3 a short hydrophobic region; exons 4 and 5 the epidermal growth factor-like domains; and exon 6 through 8 the serine protease catalytic domain (Yoshitake et al., *Biochemistry* 1985; 24: 3736-3750).

Reports exist on experimental three-dimensional structures of hFVIIa (Pike et al., *Proc Natl Acad Sci USA* 1999; 96:8925-30 and Kemball-Cook et al., *J. Struct. Biol.* 1999; 127:213-223), of hFVIIa in complex with soluble tissue factor using X-ray crystallographic methods (Banner et al., *Nature*, 1996; 380:41 and Zhang et al., *J. Mol. Biol.,* 1999; 285: 2089), and of smaller fragments of hFVII (Muranyi et al., *Biochemistry*, 1998; 37:10605 and Kao et al., *Biochemistry*, 1999; 38:7097).

Relatively few protein-engineered variants of FVII have been reported (Dickinson & Ruf, *J Biol Chem*, 1997; 272: 19875-19879, Kemball-Cook et al., *J Biol Chem*, 1998; 273: 8516-8521, Bharadwaj et al., *J Biol Chem*, 1996; 271:30685-30691, Ruf et al., *Biochemistry*, 1999; 38:1957-1966).

Reports exist on expression of FVII in BHK or other mammalian cells (WO 92/15686, WO 91/11514 and WO 88/10295) and co-expression of FVII and kex2 endoprotease in eukaryotic cells (WO 00/28065).

Commercial preparations of recombinant human FVIIa (rhFVIIa) are sold under the tradename NOVOSEVEN®. NOVOSEVEN® is indicated for the treatment of bleeding episodes in hemophilia A or B patients. NOVOSEVEN® is the only rhFVIIa for effective and reliable treatment of bleeding episodes available on the market.

An inactive form of FVII in which arginine 152 and/or isoleucine 153 are modified has been reported in WO 91/11514. These amino acids are located at the activation site. WO 96/12800 describes inactivation of FVIIa by a serine proteinase inhibitor; inactivation by carbamylation of FVIIa at the α-amino acid group I153 has been described by Petersen et al., *Eur J Biochem*, 1999; 261:124-129. The inactivated form is capable of competing with hFVII or hFVIIa for binding to TF and inhibiting clotting activity. The inactivated form of FVIIa is suggested to be used for treatment of patients suffering from hypercoagulable states, such as patients with sepsis, at risk of myocardial infarction or of thrombotic stroke.

WO 98/32466 suggests that FVII, among many other proteins, may be PEGylated (i.e. attached to one or more polyethylene glycol molecules) but does not contain any further information in this respect.

WO 01/58935 discloses a new strategy for developing FVII or FVIIa molecules having inter alia an increased half-life by means of directed glycosylation or PEGylation.

WO 03/093465 discloses FVII or FVIIa variants having certain modifications in the Gla domain and having one or more N-glycosylation sites introduced outside the Gla domain.

A circulating rhFVIIa half-life of 2.3 hours was reported in "Summary Basis for Approval for NOVOSEVEN®", FDA reference number 96-0597. Relatively high doses of frequent administration are necessary to reach and sustain the desired therapeutic or prophylactic effect. As a consequence, adequate dose regulation is difficult to obtain and the need for frequent intravenous administrations imposes restrictions on the patient's way of living.

In normal hemostasis, the procoagulant system is in balance with anticoagulant systems involved in the termination of the hemostatic reaction and the fibrinolytic system, which dissolves clots once they are formed. The anticoagulant systems contain several protease inhibitors, e.g., the Tissue Factor Pathway Inhibitor (TFPI), antithombin-III (AT-III), heparin cofactor-II (HC-II), and the protein C pathway.

TFPI is a reversible, active site-directed inhibitor of FXa, which regulates coagulation by inhibiting FVIIa-TF in a FXa-dependent manner. The TFPI-FXa complex binds to the FVIIa-TF complex, resulting in the formation of a TF-FVIIa-TFPI-FXa complex.

The in vivo relevance of TFPI is supported by experiments showing a hemostatic effect of a neutralizing anti-TFPI antibody in a hemophilia bleeding model (Erhardtsen et al. *Blood Coagul Fibrinolysis* 1995; 6:388-394). Furthermore, in biochemical reconstitution experiments, TFPI was shown to extend the initiation phase and reduce the rate of thrombin generation during the propagation phase (van't Veer and Mann; *J. Biol. Chem.* 1997; 272: 4367-4377).

An object of the present invention is to provide FVII or FVIIa variants which exhibit an increased clotting activity as compared to hFVIIa or rhFVIIa. It is contemplated that this may be obtained by way of FVII or FVIIa variants having an altered affinity to TFPI.

Another problem in current rhFVIIa treatment is the relative instability of the molecule with respect to proteolytic degradation. Proteolytic degradation is a major obstacle for obtaining a preparation in solution as opposed to a lyophilized product. The advantage of obtaining a stable soluble preparation lies in easier handling for the patient, and, in the case of emergencies, quicker action, which potentially can become life saving. Attempts to prevent proteolytic degradation by site directed mutagenesis at major proteolytic sites have been disclosed in WO 88/10295.

Thus, a further object of the present invention is to provide FVII/FVIIa variants which, in addition to the above-mentioned improved properties, are more stable towards proteolytic degradation, i.e. possess reduced sensitivity to proteolytic degradation.

A molecule with a longer circulation half-life would decrease the number of necessary administrations. Given the association of current FVIIa product with frequent injections, and the potential for obtaining more optimal therapeutic FVIIa levels with concomitant enhanced therapeutic effect, there is a clear need for improved FVII- or FVIIa-like molecules. One way to increase the circulation half-life of a protein is to ensure that renal clearance of the protein is reduced. This may be achieved by conjugating the protein to a chemical moiety which is capable of conferring reduced renal clearance to the protein. Furthermore, attachment of a chemical moiety to the protein or substitution of amino acids exposed to proteolysis may effectively block a proteolytic enzyme from contact leading to proteolytic degradation of the protein. Polyethylene glycol (PEG) is one such chemical moiety that has been used in the preparation of therapeutic protein products.

Thus, a further objective of the present invention is to provide FVII/FVIIa variants which, in addition to the above-mentioned improved properties, possess an increased functional in vivo half-life and/or an increased serum half-life.

The improved FVII/FVIIa variants disclosed herein address these objectives.

BRIEF DISCLOSURE OF THE INVENTION

The present invention provides improved recombinant FVII or FVIIa variants comprising at least one amino acid modification in a position selected from the group consisting of 196, 237 and 341. These amino acid modifications result in an altered binding of FVIIa to TFPI. As indicated above, the resulting molecules have one or more improved properties as compared to commercially available rhFVIIa, such as NOVOSEVEN®.

In interesting embodiments, the FVII or FVIIa variant has been further modified so that the resulting variant has an enhanced phospholipid membrane binding affinity, increased functional in vivo half-life, increased plasma half-life and/or an increased Area Under the Curve when administered intravenously ($AUC_{iv}$). Medical treatment with such a variant is contemplated to offer one or more advantages over the currently available rhFVIIa compound, such as lower dosage, faster action in uncontrolled bleedings and, optionally, longer duration between injections.

Accordingly, in a first aspect the invention relates to a variant of FVII or FVIIa, wherein said variant comprises at least one amino acid modification in a position selected from the group consisting of 196, 237 and 341 as compared to hFVII or hFVIIa (SEQ ID NO:2).

Another aspect of the invention relates to a nucleotide sequence encoding the variant of the invention.

In a further aspect the invention relates to an expression vector comprising the nucleotide sequence of the invention.

In a still further aspect the invention relates to a host cell comprising the nucleotide sequence of the invention or the expression vector of the invention.

In an even further aspect the invention relates to a pharmaceutical composition comprising the variant of the invention, and a pharmaceutically acceptable carrier or excipient.

Still another aspect of the invention relates to a variant of the invention, or a pharmaceutical composition of the invention, for use as a medicament.

Further aspects of the present invention will be apparent from the below description as well as from the appended claims.

BRIEF DESCRIPTION OF THE DRAWINGS

FIG. 1 shows the clotting time vs. concentration for [G237GAA]rhFVIIa when assayed in the "Whole Blood Assay". For comparison, the result from rhFVIIa is included.

DETAILED DISCLOSURE OF THE INVENTION

Definitions

In the context of the present application and invention the following definitions apply:

The term "conjugate" (or interchangeably "conjugated polypeptide variant") is intended to indicate a heterogeneous (in the sense of composite or chimeric) molecule formed by the covalent attachment of one or more polypeptide(s) to one or more non-polypeptide moieties such as polymer molecules, lipophilic compounds, sugar moieties or organic derivatizing agents. Preferably, the conjugate is soluble at relevant concentrations and conditions, i.e. soluble in physiological fluids such as blood. Examples of conjugated polypeptide variants of the invention include glycosylated and/or PEGylated polypeptides.

The term "covalent attachment" or "covalently attached" means that the polypeptide variant and the non-polypeptide moiety are either directly covalently joined to one another, or else are indirectly covalently joined to one another through an intervening moiety or moieties, such as a bridge, spacer, or linkage moiety or moieties.

When used herein, the term "non-polypeptide moiety" means a molecule that is capable of conjugating to an attachment group of the polypeptide variant of the invention. Preferred examples of such molecules include polymer molecules, sugar moieties, lipophilic compounds, or organic derivatizing agents, in particular sugar moieties. When used in the context of a polypeptide variant of the invention it will be understood that the non-polypeptide moiety is linked to the polypeptide part of the polypeptide variant through an attachment group of the polypeptide variant. As explained above, the non-polypeptide moiety may be directly covalently joined to the attachment group or it may be indirectly covalently joined to the attachment group through an intervening moiety or moieties, such as a bridge, spacer, or linkage moiety or moieties.

The "polymer molecule" is a molecule formed by covalent linkage of two or more monomers, wherein none of the monomers is an amino acid residue, except where the polymer is human albumin or another abundant plasma protein. The term "polymer" may be used interchangeably with the term "polymer molecule". The term is also intended to cover carbohydrate molecules attached by in vitro glycosylation, i.e. a synthetic glycosylation performed in vitro normally involving covalently linking a carbohydrate molecule to an attachment group of the polypeptide variant, optionally using a cross-linking agent. In vitro glycosylation is discussed in detail further below.

The term "sugar moiety" is intended to indicate a carbohydrate-containing molecule comprising one or more monosaccharide residues, capable of being attached to the polypeptide variant (to produce a polypeptide variant conjugate in the form of a glycosylated polypeptide variant) by way of in vivo glycosylation. The term "in vivo glycosylation" is intended to mean any attachment of a sugar moiety occurring in vivo, i.e. during posttranslational processing in a glycosylating cell used for expression of the polypeptide variant, e.g. by way of N-linked or O-linked glycosylation. The exact oligosaccharide structure depends, to a large extent, on the glycosylating organism in question.

An "N-glycosylation site" has the sequence N-X-S/T/C, wherein X is any amino acid residue except proline, N is asparagine and S/T/C is either serine, threonine or cysteine, preferably serine or threonine, and most preferably threonine. Preferably, the amino acid residue in position +3 relative to the asparagine residue is not a proline residue.

An "O-glycosylation site" is the OH-group of a serine or threonine residue.

The term "attachment group" is intended to indicate a functional group of the polypeptide variant, in particular of an amino acid residue thereof or a carbohydrate moiety, capable of attaching a non-polypeptide moiety such as a polymer molecule, a lipophilic molecule, a sugar moiety or an organic derivatizing agent. Useful attachment groups and their matching non-polypeptide moieties are apparent from the table below.

| Attachment group | Amino acid | Examples of non-polypeptide moiety | Conjugation method/-Activated PEG | Reference |
|---|---|---|---|---|
| —NH$_2$ | N-terminal, Lys | Polymer, e.g. PEG, with amide or imine group | mPEG-SPA Tresylated mPEG | Nektar Therapeutics Delgado et al, Critical reviews in Therapeutic Drug Carrier Systems 9(3, 4): 249–304 (1992) |
| —COOH | C-terminal, Asp, Glu | Polymer, e.g. PEG, with ester or amide group | mPEG-Hz | Nektar Therapeutics |
|  |  | Carbohydrate moiety | In vitro coupling |  |
| —SH | Cys | Polymer, e.g. PEG, with disulfide, maleimide or vinylsulfone group | PEG-vinylsulphone PEG-maleimide | Nektar Therapeutics Delgado et al, Critical reviews in Therapeutic Drug |
|  |  | Carbohydrate moiety | In vitro coupling | Carrier Systems 9(3, 4): 249–304 (1992) |
| —OH | Ser, Thr, Lys, OH— | Sugar moiety | In vivo O-linked glycosylation |  |
|  |  | PEG with ester, ether, carbamate, carbonate |  |  |
| —CONH$_2$ | Asn as part of an N-glycosylation site | Sugar moiety | In vivo N-glycosylation |  |
|  |  | Polymer, e.g. PEG |  |  |
| Aromatic residue | Phe, Tyr, Trp | Carbohydrate moiety | In vitro coupling |  |
| —CONH$_2$ | Gln | Carbohydrate moiety | In vitro coupling | Yan and Wold, Biochemistry, 1984, Jul 31; 23(16): 3759–65 |
| Aldehyde Ketone | Oxidized oligosaccharide | Polymer, e.g. PEG, PEG-hydrazide | PEGylation | Andresz et al., 1978, Macromol. Chem. 179: 301, WO 92/16555, WO 00/23114 |
| Guanidino | Arg | Carbohydrate moiety | In vitro coupling | Lundblad and Noyes, Chemical Reagents for Protein Modification, CRC Press Inc., Florida, USA |
| Imidazole ring | His | Carbohydrate moiety | In vitro coupling | As for guanidine |

For in vivo N-glycosylation, the term "attachment group" is used in an unconventional way to indicate the amino acid residues constituting a N-glycosylation site (with the sequence N-X-S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site are present. Accordingly, when the non-polypeptide moiety is a sugar moiety and the conjugation is to be achieved by in vivo N-glycosylation, the term "amino acid residue comprising an attachment group for the non-polypeptide moiety" as used in connection with alterations of the amino acid sequence of the polypeptide variant is to be understood as meaning that one or more amino acid residues constituting an in vivo N-glycosylation site are to be altered in such a manner that either a functional in vivo N-glycosylation site is introduced into the amino acid sequence or removed from said sequence.

In the present application, amino acid names and atom names (e.g. CA, CB, CD, CG, SG, NZ, N, O, C, etc) are used as defined by the Protein DataBank (PDB) (www.pdb.org) based on the IUPAC nomenclature (IUPAC Nomenclature and Symbolism for Amino Acids and Peptides (residue names, atom names, etc.), *Eur. J Biochem.*, 138, 9-37 (1984) together with their corrections in *Eur. J Biochem.*, 152, 1 (1985)).

The term "amino acid residue" is intended to include any natural or synthetic amino acid residue, and is primarily intended to indicate an amino acid residue contained in the group consisting of the 20 naturally occurring amino acids, i.e. selected from the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terminology used for identifying amino acid positions is illustrated as follows: G124 indicates that position 124 is occupied by a glycine residue in the amino acid sequence shown in SEQ ID NO:2. G124R indicates that the glycine residue of position 124 has been substituted with an arginine residue. Alternative substitutions are indicated with a "/", e.g. N145S/T means an amino acid sequence in which asparagine in position 145 is substituted with either serine or threonine. Multiple substitutions are indicated with a "+", e.g. K143N+N145S/T means an amino acid sequence which comprises a substitution of the lysine residue in position 143 with an asparagine residue and a substitution of the asparagine residue in position 145 with a serine or a threonine residue. Insertion of an additional amino acid residue, such as insertion of an alanine residue after G124 is indicated by G124GA. Insertion of two additional alanine residues after G124 is indicated by G124GAA, etc. When used herein, the term "inserted in position X" or "inserted at position X" means that the amino acid residue(s) is (are) inserted between amino acid residue X and X+1. A deletion of an amino acid residue is indicated by an asterix. For example, deletion of the glycine residue in position 124 is indicated by G124*. Unless otherwise indicated, the numbering of amino acid residues made herein is made relative to the amino acid sequence of hFVII/hFVIIa (SEQ ID NO:2).

The term "differs from" as used in connection with specific mutations is intended to allow for additional differences being present apart from the specified amino acid difference. For instance, in addition to the specified modifications in positions 196, 237 and 341, the FVII or FVIIa polypeptide variant may comprise other substitutions. Examples of such additional modifications or differences may include truncation of the N- and/or C-terminus by one or more amino acid residues (e.g. by 1-10 amino acid residues), or addition of one or more extra residues at the N- and/or C-terminus, e.g. addition of a methionine residue at the N-terminus or addition of a cysteine residue near or at the C-terminus, as well as "conservative amino acid substitutions", i.e. substitutions performed within groups of amino acids with similar characteristics, e.g. small amino acids, acidic amino acids, polar amino acids, basic amino acids, hydrophobic amino acids and aromatic amino acids.

Examples of such conservative substitutions are shown in the below table.

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Histidine (H) | Lysine (K) | |
| 5 | Isoleucine (I) | Leucine (L) | Methionine (M) | Valine (V) |
| 6 | Phenylalanine (F) | Tyrosine (Y) | Tryptophan (W) | |

Still other examples of additional modifications include modifications giving rise to an increased functional in vivo half-life, an increased serum half-life or an increased $AUC_{iv}$. Specific examples of such modifications are given further below. Moreover, the polypeptide variant of the invention may contain additional modifications giving rise to an enhanced phospholipid membrane binding affinity. Specific examples of such modifications are also given further below.

The term "variant" or "polypeptide variant" (of hFVII or hFVIIa) is intended to cover a polypeptide which differs in one or more amino acid residues from SEQ ID NO:2, normally in 1-15 amino acid residues (for example in 1, 2, 3, 4, 5, 6, 7, 8, 9, 10, 11, 12, 13, 14 or 15 amino acid residues), e.g. in 1-10, 1-8, 1-6, 1-5, 1-4 or 1-3 amino acid residues, e.g. one or two amino acid residues. In the present context, the term "modification" encompasses insertions, deletions, substitutions and combinations thereof. It will be understood that a polypeptide variant according to the present invention will be modified in at least one of the following positions: 196, 237 and/or 314.

The term "nucleotide sequence" is intended to indicate a consecutive stretch of two or more nucleotide molecules. The nucleotide sequence may be of genomic, cDNA, RNA, semisynthetic, synthetic origin, or any combinations thereof "Cell", "host cell", "cell line" and "cell culture" are used interchangeably herein and all such terms should be understood to include progeny resulting from growth or culturing of a cell.

"Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. Generally, "operably linked" means that the nucleotide sequences being linked are contiguous and, in the case of a secretory leader, contiguous and in reading phase.

The terms "mutation" and "substitution" are used interchangeably herein.

In the context of the present invention the terms "modification" or "amino acid modification" are intended to cover replacement of an amino acid side chain, substitution of an amino acid residue, deletion of an amino acid residue and insertion of an amino acid residue.

The term "introduce" refers to introduction of an amino acid residue, in particular by substitution of an existing amino acid residue, or alternatively by insertion of an additional amino acid residue.

The term "remove" refers to removal of an amino acid residue, in particular by substitution of the amino acid residue to be removed by another amino acid residue, or alternatively by deletion (without substitution) of the amino acid residue to be removed.

The term "FVII" or "FVII polypeptide" refers to a FVII molecule provided in single chain form.

The term "FVIIa" or "FVIIa polypeptide" refers to a FVIIa molecule provided in its activated two-chain form. When the amino acid sequence of SEQ ID NO:2 is used to describe the amino acid sequence of FVIIa it will be understood that the peptide bond between R152 and I153 of the single-chain form has been cleaved, and that one of the chains comprises amino acid residues 1-152, the other chain amino acid residues 153-406.

The terms "rFVII" and "rFVIIa" refer to FVII and FVIIa polypeptides produced by recombinant techniques.

The terms "hFVII" and "hFVIIa" refer to human wild-type FVII and FVIIa, respectively, having the amino acid sequence shown in SEQ ID NO:2

The terms "rhFVII" and "rhFVIIa" refer to human wild-type FVII and FVIIa, having the amino acid sequence shown in SEQ ID NO:2, produced by recombinant means. An example of rhFVIIa is NovoSeven®.

The term "TF" means Tissue Factor.

The term "TFPI" means Tissue Factor Pathway Inhibitor.

The term "FX" means Factor X.

The term "Gla domain" is used about the first about 45 amino acid residues counted from the N-terminus.

The term "protease domain" is used about residues 153-406 counted from the N-terminus.

The term "catalytic site" is used to mean the catalytic triad consisting of S344, D242 and H193 of the polypeptide variant.

The term "amidolytic activity" is intended to mean the activity measured in the "Amidolytic Assay" described herein. In order to exhibit "amidolytic activity" a variant of the invention, in its activated form, should have at least 10% of the amidolytic activity of rhFVIIa when assayed in the "Amidolytic Assay" described herein. In a preferred embodiment of the invention the variant, in its activated form, has at least 20% of the amidolytic activity of rhFVIIa, such as at least 30%, e.g. at least 40%, more preferably at least 50%, such as at least 60%, e.g. at least 70%, even more preferably at least 80%, such as at least 90% of the amidolytic activity of rhFVIIa when assayed in the "Amidolytic Assay" described herein. In an interesting embodiment the variant, in its activated form, has substantially the same amidolytic activity as rhFVIIa, such as an amidolytic activity of 75-125% of the amidolytic activity of rhFVIIa.

The term "clotting activity" is used to mean the activity measured in the "Whole Blood Assay" described herein. It will be understood that the activity measured in the "Whole Blood Assay" is the time needed to obtain clot formation. Thus, a lower clotting time corresponds to a higher clotting activity.

The term "increased clotting activity" is used to indicate that the clotting time of the polypeptide variant is statistically significantly decreased relative to that generated by rhFVIIa as determined under comparable conditions and when measured in the "Whole Blood Assay" described herein.

The term "immunogenicity" as used in connection with a given substance is intended to indicate the ability of the substance to induce a response from the immune system. The immune response may be a cell or antibody mediated response (see, e.g., Roitt: Essential Immunology (8th Edition, Blackwell) for further definition of immunogenicity). Normally, reduced antibody reactivity will be an indication of reduced immunogenicity. The reduced immunogenicity may be determined by use of any suitable method known in the art, e.g. in vivo or in vitro.

The term "functional in vivo half-life" is used in its normal meaning, i.e. the time at which 50% of the biological activity of the polypeptide variant is still present in the body/target organ, or the time at which the amidolytic or clotting activity of the polypeptide variant is 50% of the initial value.

As an alternative to determining functional in vivo half-life, "serum half-life" may be determined, i.e. the time at which 50% of the polypeptide variant circulates in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life". The polypeptide variant is cleared by the action of one or more of the reticuloendothelial systems (RES), kidney, spleen or liver, by tissue factor, SEC receptor or other receptor mediated elimination, or by specific or unspecific proteolysis. Normally, clearance depends on size (relative to the cutoff for glomerular filtration), charge, attached carbohydrate chains, and the presence of cellular receptors for the protein. The functionality to be retained is normally selected from procoagulant, proteolytic or receptor binding activity. The functional in vivo half-life and the serum half-life may be determined by any suitable method known in the art.

The term "increased" as used about the functional in vivo half-life or serum half-life is used to indicate that the relevant half-life of the polypeptide variant is statistically significantly increased relative to that of a reference molecule, such as a rhFVIIa as determined under comparable conditions (typically determined in an experimental animal, such as rats, rabbits, pigs or monkeys).

The term "$AUC_{iv}$" or "Area Under the Curve when administered intravenously" is used in its normal meaning, i.e. as the area under the activity in serum-time curve, where the polypeptide variant has been administered intravenously, in particular when administered intravenously in rats. Once the experimental activity-time points have been determined, the $AUC_{iv}$ may conveniently be calculated by a computer program, such as GraphPad Prism 3.01.

The term "reduced sensitivity to proteolytic degradation" is primarily intended to mean that the polypeptide variant has reduced sensitivity to proteolytic degradation in comparison to rhFVIIa as determined under comparable conditions. Preferably, the proteolytic degradation is reduced by at least 10% (e.g. by 10-25% or by 10-50%), such as at least 25% (e.g. by 25-50%, by 25-75% or by 25-100%), more preferably by at least 35%, such as at least 50%, (e.g. by 50-75% or by 50-100%) even more preferably by at least 60%, such as by at least 75% (e.g. by 75-100%) or even at least 90%. Most preferably, the proteolytic degradation is reduced by at least 99%.

The term "renal clearance" is used in its normal meaning to indicate any clearance taking place by the kidneys, e.g. by glomerular filtration, tubular excretion or degradation in the tubular cells. Renal clearance depends on physical characteristics of the polypeptide, including size (diameter), hydrodynamic volume, symmetry, shape/rigidity, and charge. A molecular weight of about 67 kDa is often considered to be a cut-off-value for renal clearance. Renal clearance may be established by any suitable assay, e.g. an established in vivo assay. Typically, renal clearance is determined by administering a labelled (e.g. radiolabelled or fluorescence labelled) polypeptide to a patient and measuring the label activity in urine collected from the patient. Reduced renal clearance is determined relative to a corresponding reference polypeptide, e.g. rhFVIIa, under comparable conditions. Preferably, the renal clearance rate of the polypeptide variant is reduced by at least 50%, e.g. at least 75% or at least 90% compared to rhFVIIa.

Polypeptide Variants of the Invention

In its broadest aspect the present invention relates to a variant of FVII or FVIIa, wherein said variant comprises at least one amino acid modification in a position selected from the group consisting of 196, 237 and 341 as compared to hFVII or hFVIIa, preferably as compared to hFVIIa. Although the variant will typically contain a modification in one of these positions, it may also contain a modification in two of these positions, i.e. modifications in 196+237, 196+341 or 237+341, or in all three positions.

In the following sections preferred modifications in the above-mentioned positions are given.

Position 196

In one embodiment of the invention, the present invention relates to a variant of FVII or FVIIa, wherein said variant comprises at least one modification in position 196 as compared to hFVII or hFVIIa (SEQ ID NO:2).

In a preferred embodiment of the invention the modification in position 196 is a substitution, in particular D196N or D196K.

The variant will generally comprise a total of 1-15 amino acid modifications (e.g. substitutions), such as 1-10 amino acid modifications (e.g. substitutions), e.g. 1-5 amino acid modifications (e.g. substitutions) or 1-3 amino acid modifications (e.g. substitutions).

For example, the variant may contain at least one further amino acid modification made in the Gla domain as explained in the section entitled "Modifications in the Gla domain" below, and/or at least one further amino acid modification which leads to introduction of an in vivo N-glycosylation site as explained in the section entitled "Introduction of additional sugar moieties" below, and/or at least one further amino acid modification capable of increasing the intrinsic activity and/or at least one further amino acid modification which increases the TF-binding affinity. Examples of the latter modifications are described in the section entitled "Other modifications" below.

Position 237

In a further embodiment of the invention, the present invention relates to a variant of FVII or FVIIa, wherein said variant comprises at least one modification in position 237 as compared to hFVII or hFVIIa (SEQ ID NO:2).

In a preferred embodiment of the invention the modification in position 237 is a substitution, in particular G237L.

The variant will generally comprise a total of 1-15 amino acid modifications (e.g. substitutions), such as 1-10 amino acid modifications (e.g. substitutions), e.g. 1-5 amino acid modifications (e.g. substitutions) or 1-3 amino acid modifications (e.g. substitutions).

For example, the variant may contain at least one further amino acid modification made in the Gla domain as explained in the section entitled "Modifications in the Gla domain" below, and/or at least one further amino acid modification which leads to introduction of an in vivo N-glycosylation site as explained in the section entitled "Introduction of additional sugar moieties" below, and/or at least one further amino acid modification capable of increasing the intrinsic activity and/or at least one further amino acid modification which increases the TF-binding affinity. Examples of the latter modifications are described in the section entitled "Other modifications" below.

In still another embodiment of the invention the modification in position 237 is an insertion. In an interesting embodiment the insertion is selected from the group consisting of G237GXX, G237GXXX and G237GXXXX, wherein X is any amino acid residue. Preferably, X is selected from the group consisting of Ala, Val, Leu, Ile, Gly, Ser, Thr, in particular Ala. Specific examples of preferred insertions include G237GAA, G237GAAA (GAAA, SEQ ID NO:20) and G237GAAAA (GAAAA, SEQ ID NO:21). Most preferably, the insertions are G237GAA.

Position 341

In a still further embodiment of the invention, the present invention relates to a variant of FVII or FVIIa, wherein said variant comprises at least one modification in position 341 as compared to hFVII or hFVIIa (SEQ ID NO:2).

In a preferred embodiment of the invention the modification in position 341 is a substitution, such as K341N or K341Q, in particular K341Q.

The variant will generally comprise a total of 1-15 amino acid modifications (e.g. substitutions), such as 1-10 amino acid modifications (e.g. substitutions), e.g. 1-5 amino acid modifications (e.g. substitutions) or 1-3 amino acid modifications (e.g. substitutions).

For example, the variant may contain at least one further amino acid modification made in the Gla domain as explained in the section entitled "Modifications in the Gla domain" below, and/or at least one further amino acid modification which leads to introduction of an in vivo N-glycosylation site as explained in the section entitled "Introduction of additional sugar moieties" below, and/or at least one further amino acid modification capable of increasing the intrinsic activity and/or at least one further amino acid modification which increases the TF-binding affinity. Examples of the latter modifications are described in the section entitled "Other modifications" below.

Properties of the Variants of the Invention

The variants disclosed may have an altered affinity for TFPI, which may be assessed using the BIAcore® Assays described herein. Using the BIAcore® assays it is possible to estimate various kinetic binding constants, such as the equilibrium dissociation constant, $K_D$, where $K_D=k_d/k_a$, where $k_a$ is the association rate constant and $k_d$ is the dissociation rate constant. It will be understood that a higher value of $K_D$ corresponds to a decreased affinity for TFPI.

The variants of the invention possess an increased clotting activity (or a reduced clotting time) as compared to hFVIIa or rhFVIIa. In a preferred embodiment of the invention the ratio between the time to reach clot formation for the variant ($t_{variant}$) and the time to reach clot formation for hFVIIa or rhFVIIa ($t_{wt}$) is at the most 0.9 when assayed in the "Whole Blood Assay" described herein. More preferably the ratio ($t_{variant}/t_{wt}$) is at the most 0.75, such as 0.7, even more preferably the ratio ($t_{variant}/t_{wt}$) is at the most 00.6, most preferably the ratio ($t_{variant}/t_{wt}$) is at the most 0.5 when assayed in the "Whole Blood Assay" described herein.

Further Modifications

As indicated above the FVII or FVIIa variant of the invention may comprise further modifications aimed at conferring additional advantageous properties to the FVII or FVIIa molecule, e.g. at least one further amino acid substitution.

In order to avoid too much disruption of the structure and function of the FVII or FVIIa polypeptide, the FVII or FVIIa polypeptide variant of the invention will typically have an amino acid sequence having more than 95% identity with SEQ ID NO:2, preferably more than 96% identity with SEQ ID NO:2, such as more than 97% identity with SEQ ID NO:2, more preferably at least 98% identity with SEQ ID NO:2, such as more than 99% identity with SEQ ID NO:2. Amino acid sequence homology/identity is conveniently determined from aligned sequences, using e.g. the ClustalW program, version 1.8, June 1999, using default parameters (Thompson et al., 1994, ClustalW: Improving the sensitivity of progressive multiple sequence alignment through sequence weighting, position-specific gap penalties and weight matrix choice, Nucleic Acids Res., 22: 4673-4680) or from the PFAM families database version 4.0 (http://pfam.wustl.edu/) (Nucleic Acids Res. 1999 Jan. 1; 27(1):260-2) by use of GENEDOC version 2.5 (Nicholas et al., 1997 GeneDoc: Analysis and Visualization of Genetic Variation, EMBNEW.NEWS 4:14; Nicholas, K. B. and Nicholas H. B. Jr. 1997 GeneDoc: Analysis and Visualization of Genetic Variation).

Modifications in the Gla Domain

In an interesting embodiment of the invention, at least one further amino acid modification is made in the Gla domain, i.e. within the first about 45 amino acid residues counted from the N-terminus of the FVII or FVIIa molecule. Preferably, no modifications are made in residues 6, 7, 14, 16, 19, 20, 25, 26, 29 and 35.

Without being limited by any particular theory, it is presently believed that an increased clotting activity may be achieved by an enhanced binding affinity of the FVIIa molecule to the phospholipid membranes present on the surface of activated platelets. This enhanced affinity is believed to result in a higher local concentration of the activated FVIIa polypeptide in close proximity to the other coagulation factors, particularly FX. Thus, the rate of activation of FX to FXa will be higher, simply due to a higher molar ratio of the activated FVII polypeptide to FX. The increased activation rate of FX then results in a higher amount of active thrombin, and thus a higher rate of cross-linking of fibrin.

Thus, in a preferred embodiment according to this aspect of the invention, the polypeptide variant has, in its activated form, an enhanced phospholipid membrane binding affinity relative to the rhFVIIa polypeptide. Phospholipid membrane binding affinity may be measured by methods known in the art, such as by the BIAcore® assays described in K. Nagata and H. Handa (Ads.), Real-Time Analysis of Biomolecular Interactions, Springer-Verlag, Tokyo, 2000, Chapter 6 entitled "Lipid-Protein Interactions".

A number of modifications in the FVII Gla domain leading to an increased membrane binding affinity have been described in the art (see, for example, WO 99/20767 and WO 00/66753). Particular interesting positions in the Gla domain to be modified are positions P10, K32, D33, A34 as well as insertion of an amino acid residue between A3 and F4. Thus, in a preferred embodiment of the invention, the variant comprises, in addition to one or more of the modifications mentioned above a substitution in a position selected from the group consisting of P10, K32, D33 and A34 and combinations thereof as well as an insertion between A3 and F4. Particularly preferred positions are P10 and K32.

Preferably, the substitution to be made in position 32 is K32E, the substitution to be made in position 10 is P10Q, the substitution to be made in position 33 is D33F, the substitution to be made in position 34 is A34E and the insertion between A3 and F4 is preferably A3AY. In an interesting embodiment of the invention the variant comprises at least one of the following further modifications: A3AY, P10Q, K32E, D33F, A34E or combinations thereof Most preferably, the variant comprises one of the following further modifications: K32E, P10Q+K32E, A3AY+P10Q+K32E+D33F+A34E.

Introduction of Non-Polypeptide Moieties

In another embodiment, the FVII or FVIIa variant has been further modified so that the resulting polypeptide variant has increased functional in vivo half-life and/or increased plasma half-life and/or increased increased Area Under the Curve when administered intravenously ($AUC_{iv}$), in particular when administered intravenously in rats, and/or increased bioavailability and/or reduced sensitivity to proteolytic degradation. Medical treatment with a polypeptide variant according to this aspect of the invention may offer a number of advantages over the currently available rFVIIa compound, such as lower dosage and, optionally, longer duration between injections. Numerous examples of relevant amino acid substitutions are given in WO 01/58935.

The variants disclosed in WO 61/58935 are the result of a generally new strategy for developing improved FVII or FVIIa molecules. This strategy, in which non-polypeptide moieties are attached to FVII/FVIIa variants, may also be used for the FVII or FVIIa variants of the present invention. More specifically, by removing and/or introducing an amino acid residue comprising an attachment group for a non-polypeptide moiety in the FVII or FVIIa polypeptide variant of the invention, it is possible to specifically adapt the polypeptide variant so as to make the molecule more susceptible to conjugation to a non-polypeptide moiety of choice, to optimize the conjugation pattern (e.g. to ensure an optimal distribution and number of non-polypeptide moieties on the surface of the FVII or FVIIa polypeptide variant and to ensure that only the attachment groups intended to be conjugated are present in the molecule) and thereby obtain a new conjugate molecule, which has activity and in addition one or more improved properties as compared to the FVII and FVIIa molecules available today. For instance, when the total number of amino acid residues comprising an attachment group for the non-polypeptide of choice is increased or decreased to an optimized level, the renal clearance of the conjugate is typically significantly reduced due to the altered shape, size and/or charge of the molecule achieved by the conjugation.

Thus, interesting polypeptide variants according to this aspect of the present invention are such polypeptides wherein at least one amino acid residue comprising an attachment group for a non-polypeptide moiety has been introduced or removed in a FVII or FVIIa polypeptide variant as described elsewhere herein.

In interesting embodiments of the present invention more than one amino acid residue of the FVII or FVIIa polypeptide variant is altered, e.g. the alteration embraces removal as well as introduction of amino acid residues comprising an attachment group for the non-polypeptide moiety of choice. In addition to the removal and/or introduction of amino acid residues the polypeptide variant may comprise other substitutions or glycosylations that are not related to introduction and/or removal of amino acid residues comprising an attachment group for the non-polypeptide moiety. Also, the polypeptide variant may be attached, e.g., to a serine proteinase inhibitor to inhibit the catalytic site of the polypeptide.

The amino acid residue comprising an attachment group for a non-polypeptide moiety, whether it be removed or introduced, is selected on the basis of the nature of the non-polypeptide moiety of choice and, in most instances, on the basis of the method in which conjugation between the polypeptide variant and the non-polypeptide moiety is to be achieved. For instance, when the non-polypeptide moiety is a polymer molecule such as a polyethylene glycol or polyalkylene oxide derived molecule, amino acid residues comprising an attachment group may be selected from the group consisting of lysine, cysteine, aspartic acid, glutamic acid, histidine, and tyrosine, preferably lysine, cysteine, aspartic acid and glutamic acid, more preferably lysine and cysteine, in particular cysteine.

Whenever an attachment group for a non-polypeptide moiety is to be introduced into or removed from the FVII or FVIIa polypeptide variant, the position of the amino acid residue to be modified is preferably located at the surface of the FVII or FVIIa polypeptide, and more preferably occupied by an amino acid residue which has more than 25% of its side chain exposed to the surface (as defined in WO 01/58935 and in Example 1 herein), preferably more than 50% of its side chain exposed to the surface (as defined in WO 01/58935 and in Example 1 herein).

Furthermore, the position is preferably selected from a part of the FVII molecule that is located outside the tissue factor binding site, the Gla domain, the active site region and/or the ridge of the active site binding cleft These sites/regions are identified in Example 1 herein.

The polypeptide variant of the invention may contain 1-10 non-polypeptide moieties, typically 1-8 or 2-8 non-polypeptide moieties, preferably 1-5 or 2-5 non-polypeptide moieties, such as 1-4 or 1-3 non-polypeptide moieties, e.g. 1, 2 or 3 non-polypeptide moieties, in particular PEG, such as mPEG or sugar moieties.

Further details regarding introduction of non-polypeptide moieties may be found in WO 01/58935, incorporated by reference.

Introduction of Additional Sugar Moieties

In an interesting embodiment of the invention the non-polypeptide moiety is a sugar moiety, i.e., the polypeptide variant of the invention is one which, in addition to one or more of the modifications described elsewhere herein comprises at least one sugar moiety covalently attached to an introduced glycosylation site. Preferably said glycosylation site is an in vivo glycosylation site, in particular an in vivo N-glycosylation site, which has been introduced by substitution. Preferably, said glycosylation site is introduced in a position located outside the Gla domain, the tissue factor binding site, the active site region and the ridge of the active site binding cleft.

When used in the present context, the term "naturally occurring glycosylation site" covers the glycosylation sites at positions N145, N322, S52 and S60. In a similar way, the term "naturally occurring in vivo O-glycosylation site" includes the positions S52 and S60, whereas the term "naturally occurring in vivo N-glycosylation site" includes positions N145 and N322.

Thus, in a very interesting embodiment of the invention, the non-polypeptide moiety is a sugar moiety and the introduced attachment group is a glycosylation site, preferably an in vivo glycosylation site, such as an in vivo O-glycosylation site or an in vivo N-glycosylation site, in particular an in vivo N-glycosylation site. Typically, 1-10 glycosylation sites, in particular in vivo N-glycosylation sites, have been introduced, preferably 1-8, 1-6, 14 or 1-3 glycosylation sites. In particular, 1, 2 or 3 in vivo N-glycosylation sites have been introduced, preferably by substitution.

It will be understood that in order to prepare a polypeptide variant wherein the FVII or FVII polypeptide variant comprises one or more glycosylation sites, the polypeptide variant must be expressed in a host cell capable of attaching sugar (oligosaccharide) moieties at the glycosylation site(s). Examples of glycosylating host cells are given in the section further below entitled "Coupling to a sugar moiety".

Examples of positions wherein the glycosylation sites may be introduced include, but are not limited to, positions comprising an amino acid residue having an amino acid residue having at least 25% of its side chain exposed to the surface (as defined in Example 1 herein), such as in a position comprising an amino acid residue having at least 50% of its side chain exposed to the surface (as defined in Example 1 herein). It should be understood that when the term "at least 25% (or at least 50%) of its side chain exposed to the surface" is used in connection with introduction of an in vivo N-glycosylation site this term refers to the surface accessibility of the amino acid side chain in the position where the sugar moiety is actually attached. In many cases it will be necessary to introduce a serine or a threonine residue in position +2 relative to the asparagine residue to which the sugar moiety is actually attached (unless, of course, this position is already occupied by a serine or a threonine residue) and these positions, where the serine or threonine residues are introduced, are allowed to be buried, i.e. to have less than 25% (or 50%) of their side chains exposed to the surface.

Specific examples of such substitutions creating an in vivo N-glycosylation site include a substitution selected from the group consisting of A51N, G58N, T106N, K109N, G124N, K143N+N145T, A175T, I205S, I205T, V253N, T267N, T267N+S269T, S314N+k316S, S314N+K316T, R315N+V317S, R315N+V317T, K316N+G318S, K316N+G318T, G318N, D334N and combinations thereof. In a preferred embodiment of the invention the in vivo N-glycosylation site is created by performing a substitution selected from the group consisting of A51N, G58N, T106N, K109N, G124N, K143N+N145T, A175T, I205T, V253N, T267N+S269T, S314N+K316T, R315N+V317T, K316N+G318T, G318N, D334N and combinations thereof, more preferably by a substitution selected from the group consisting of T106N, A175T, I205T, V253N, T267N+S269T and combinations thereof, in particular I205T.

In one embodiment of the invention, one in vivo N-glycosylation site site has been introduced by substitution. In another embodiment of the invention at least two in vivo N-glycosylation site sites, such as two in vivo N-glycosylation sites, have been introduced by substitution. Specific examples of substitutions creating two in vivo N-glycosylation sites include A51N+G58N, A51N+T106N, A51N+K109N, A51N+G124N, A51N+K143N+N145T, A51N+A175T, A51N+I205T, A51N+V253N, A51N+T267N+S269T, A51N+S314N+K316T, A51N+R315N+V317T, A51N+K316N+G318T, A51N+G318N, A51N+D334N, G58N+T106N, G58N+K109N, G58N+G124N, G58N+K143N+N145T, G58N+A175T, G58N+I205T, G58N+V253N, G58N+T267N+S269T, G58N+S314N+K316T, G58N+R315 N+V317T, G58N+K316N+G318T, G58N+G318N, G58N+D334N, T106N+K109N, T106N+G124N, T106N+K143N+M145T, T106N+A175T, T106N+I205T, T106N+V253N, T106N+T267N+S269T, T106N+S314N+K316T, T106N+R315N+V317T, T106N+K316N+G318T, T106N+G318N, T106N+D334N, K109N+G124N, K109N+

K143N+N145T, K109N+A175T, K109N+I205T, K109N+ V253N, K109N+T267N+S269T, K109N+S314N+K316T, K109N+R315N+V317T, K109N+K316N+G318T, K109N+ G318N, K109N+D334N, G124N+K143N+N145T, G124N+ A175T, G124N+I205T, G124N+V253N, G124N+T267N+ S269T, G124N+S314N+K316T, G124N+R315N+V317T, G124N+K316N+G318T, G124N+G318N, G124N+D334N, K143N+N145T+A175T, K143N+N145T+I205T, K143N+ N145T+V253N, K143N+N145T+T267N+S269T, K143N+ N145T+S314N+K316T, K143N+N145T+R315N+V317T, K143N+N145T+K316N+G318T, K143N+N145T+G318N, K143N+N145T+D334N, A175T+I205T, A175T+V253N, A175T+T267N+S269T, A175T+S314N+K316T, A175T+ R315N+V317T, A175T+K316N+G318T, A175T+G318N, A175T+D334N, I205T+V253N, I205T+T267N+S269T, I205T+S314N+K316T, I205T+R315N+V317T, I205T+ K316N+G318T, I205T+G318N, I205T+D334N, V253N+ T267N+S269T, V253N+S314N+K316T, V253N+R315N+ V317T, V253N+K316N+G318T, V253N+G318N, V253N+ D334N, T267N+S269T+S314N+K316T, T267N+S269T+ R315N+V317T, T267N+S269T+K316N+G318T, T267N+ S269T+G318N, T267N+S269T+D334N, S314N+K316T+ R315N+V317T, S314N+K316T+G318N, S314N+K316T+ D334N, R315N+V317T+K316N+G318T, R315N+V317T+ G318N, R315N+V317T+D334N or G318N+D334N, preferably T106N+A175T, T106N+I205T, T106N+V253N, T106N+T267N+S269T, A175T+I205T, A175T+V253N, A175T+T267N+S269T, I205T+V253N, I205T+T267N+ S269T or V253N+T267N+S269T, more preferably T106N+ I205T, T106N+V253N or I205T+T267N+S269T.

In a still further embodiment of the invention at least three in vivo N-glycosylation site sites, such as three in vivo N-glycosylation sites, have been introduced by substitution. Specific examples of substitutions creating three in vivo N-glycosylation sites include I205T+V253N+T267N+S269T and T106N+I205T+V253N.

In addition to a sugar moiety, the polypeptide variant according to the aspect of the invention described in the present section may contain additional non-polypeptide moieties, in particular a polymer molecule, as described in the present application, conjugated to one or more attachment groups present in the FVII or FVIIa variant.

It will be understood that any of the amino acid changes, in particular substitutions, specified in this section can be combined with any of the amino acid changes, in particular substitutions, specified in the other sections herein disclosing specific amino acid changes. For instance, any of the glycosylated polypeptides variants disclosed in the present section having introduced and/or removed at least one glycosylation site may further be conjugated to a polymer molecule, such as polyethylene glycol (PEG), or any other non-polypeptide moiety.

Further information on introduction of glycosylation sites may be found in WO 01/58935 and WO 03/093465, incorporated by reference.

Introduction of Non-Polypeptide Moieties that have Cysteine as an Attachment Group In a further interesting embodiment of the invention the non-polypeptide moiety has cysteine as an attachment group, i.e., the polypeptide variant of the invention is one which, in addition to one or more of the modifications described above comprises at least one non-polypeptide moiety covalently attached to an introduced cysteine. Preferably said cysteine residue is introduced by substitution. Preferably, said cysteine residue is introduced in a position located outside the TF binding site, the Gla domain, the active site region, and the ridge of the active site binding cleft.

FVII/FVIIa contains 22 cysteine residues located outside the Gla domain and disulfide bridges are established between the following cysteine residues: C50 and C61, C55 and C70, C72 and C81, C91 and C102, C98 and C112, C114 and C127, C135 and C262, C159 and C164, C178 and C194, C310 and C329, and between C340 and C368.

Thus, in an interesting embodiment of the invention at least one cysteine residue has been introduced, preferably by substitution, in the FVII or FVIIa polypeptide variant. Typically 1-10 cysteine residues have been introduced, preferably 1-8, 1-6, 1-4 or 1-3 cysteine residues have been introduced. In particular 1, 2 or 3 cysteine residues have been introduced, preferably by substitution.

Examples of positions where the cysteine residues may be introduced include, but are not limited to, positions comprising an amino acid residue having an amino acid residue having at least 25% of its side chain exposed to the surface (as defined in Example 1 herein), such as in a position comprising an amino acid residue having at least 50% of its side chain exposed to the surface (as defined in Example 1 herein).

In an interesting embodiment of the invention, a cysteine residue is introduced near or at the C-terminus. For example, a cysteine residue may be introduced, either by substitution or insertion, in position 400-406. Specific examples of substitutions include: L400C, L401C, R402C, A403C, P404C, F405C and P406C, in particular P406C. Specific examples of insertions include L400LC, L401LC, R402RC, A403AC, P404PC, F405FC and P406PC, in particular P406PC.

While the non-polypeptide moiety according to this aspect of the invention may be any molecule which when using the given conjugation method has cysteine as an attachment group, it is preferred that the non-polypeptide moiety is a polymer molecule. The polymer molecule may be any of the molecules mentioned in the section entitled "Conjugation to a polymer molecule", but is preferably selected from the group consisting of linear or branched polyethylene glycol or another polyalkylene oxide. In a particular interesting embodiment the polymer molecule is PEG, such as vinyl sulfone polyethylene glycol (VS-PEG).

The conjugation between the polypeptide variant and the polymer may be achieved in any suitable manner, e.g. as described WO 01/58935.

When the FVII or FVIIa polypeptide variant comprises only one conjugatable cysteine residue, this residue is preferably conjugated to a non-polypeptide moiety with a molecular weight of from about 5 kDa to about 20 kDa, e.g. from about 10 kDa to about 20 kDa, such as a molecular weight of about 5 kDa, about 10 kDa, about 12 kDa, about 15 kDa or about 20 kDa, either directly conjugated or indirectly through a low molecular weight polymer (as disclosed in WO 99/55377). When the FVII or FVIIa polypeptide variant comprises two or more conjugatable cysteine residues, normally each of the non-polypeptide moieties has a molecular weight of from about 5 to about 10 kDa, such as about 5 kDa or about 10 kDa.

It will be understood that any of the amino acid changes, in particular substitutions, specified in this section can be combined with any of the amino acid modifications specified in the other sections herein.

Other Modifications

In a further embodiment of the present invention, the FVII or FVIIa variant may, in addition to the modifications described in the sections above, also contain mutations which are already known to increase the intrinsic activity of the polypeptide, e.g. those described in WO 02/22776.

Examples of preferred substitutions include substitutions selected from the group consisting of V158D, E296D, M298Q, L305V and K337A. More preferably, said substitutions are selected from the group consisting of

V158D+E296D+M298Q+L305V+K337A,

V158D+E296D+M298Q+K337A, V158D+E296D+M298Q+L305V,

V158D+E296D+M298Q,

M298Q, L305V+K337A, L305V and K337A.

Moreover, the variant may contain modifications which increase the TF binding affinity. Examples of such modifications include substitutions selected from the group consisting of L39E, L39Q, L39H, I42R, S43H, S43Q, K62E, K62R, L65Q, L65S, F71D, F71Y, F71E, F71Q, F71N, E82Q, E82N, E82K, F275H and combinations thereof, in particular L65Q, F71Y, K62E, S43Q and combinations thereof.

As already indicated above, the variant may also contain conservative amino acid substitutions.

The Non-Polypeptide Moiety

As indicated further above the non-polypeptide moiety of the polypeptide variant of the invention is preferably selected from the group consisting of a polymer molecule, a lipophilic compound, a sugar moiety (by way of in vivo glycosylation) and an organic derivatizing agent. All of these agents may confer desirable properties to the polypeptide variant, in particular increased functional in vivo half-life and/or increased plasma half-life.

The polypeptide variant is normally conjugated to only one type of non-polypeptide moiety, but may also be conjugated to two or more different types of non-polypeptide moieties, e.g. to a polymer molecule and a sugar moiety, to a lipophilic group and a sugar moiety, to an organic derivatizing agent and a sugar moiety, to a lipophilic group and a polymer molecule, etc. The conjugation to two or more different non-polypeptide moieties may be done simultaneously or sequentially. Further information on conjugation to non-polypeptide moieties is found in WO 01/58935 and WO 03/093465, incorporated by reference.

Methods of Preparing a Conjugated Polypeptide Variant of the Invention

In general, a conjugated polypeptide variant according to the invention may be produced by culturing an appropriate host cell under conditions conducive for the expression of the polypeptide, and recovering the polypeptide variant, wherein a) the polypeptide variant comprises at least one N- or O-glycosylation site and the host cell is a eukaryotic host cell capable of in vivo glycosylation, and/or b) the polypeptide variant is subjected to conjugation to a non-polypeptide moiety in vitro. See e.g. WO 01/58935 and WO 03/093465 for further information on preparation of conjugated variants of FVII.

Conjugation to a Polymer Molecule

The polymer molecule to be coupled to the polypeptide variant may be any suitable polymer molecule, such as a natural or synthetic homo-polymer or hetero-polymer, typically with a molecular weight in the range of about 300-100,000 Da, such as about 500-20,000 Da, more preferably in the range of about 500-15,000 Da, even more preferably in the range of about 2-12 kDa, such as in the range of about 3-10 kDa When the term "about" is used herein in connection with a certain molecular weight, the word "about" indicates an approximate average molecular weight and reflects the fact that there will normally be a certain molecular weight distribution in a given polymer preparation.

Examples of homo-polymers include a polyol (i.e. poly-OH), a polyamine (i.e. poly-$NH_2$) and a polycarboxylic acid (i.e. poly-COOH). A hetero-polymer is a polymer comprising different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), poly-carboxylate, poly-(vinylpyrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule, since it has only few reactive groups capable of cross-linking compared to, e.g., polysaccharides such as dextran. In particular, monofunctional PEG, e.g. methoxypolyethylene glycol (mPEG), is of interest since its coupling chemistry is relatively simple (only one reactive group is available for conjugating with attachment groups on the polypeptide). Consequently, the risk of cross-inking is eliminated, the resulting conjugated polypeptide variants are more homogeneous and the reaction of the polymer molecules with the polypeptide variant is easier to control.

To effect covalent attachment of the polymer molecule(s) to the polypeptide variant, the hydroxyl end groups of the polymer molecule must be provided in an activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succininidy carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g. from Nektar Therapeutics, Huntsville, Ala., USA, or from Poly-MASC Pharmaceuticals plc, UK. Specific examples of activated linear or branched polymer molecules for use in the present invention are described in the Nektar Molecule Engineering Catalog 2003 (Nektar Therapeutics), incorporated herein by reference.

In a particular interesting embodiment PEGylation is achieved by conjugating the PEG group(s) to introduced cysteine residues. Specific examples of activated PEG polymers particularly preferred for coupling to cysteine residues, include the following linear PEGs: vinylsulfone-PEG (VS-PEG), preferably vinylsulfone-mPEG (VS-mPEG); maleimide-PEG (MAL-PEG), preferably maleimide-mPEG (MAL-mPEG) and orthopyridyl-disulfide-PEG (OPSS-PEG), preferably orthopyridyl-disulfide-mPEG (OPSS-mPEG). Typically, such PEG or mPEG polymers will have a size of about 5 kDa, about 10 kDa, about 12 kDa or about 20 kDa.

In another embodiment, a suitable PEG molecule may be attached to the N-terminal.

Detailed information on methods and polymers that may be used for PEGylation of FVII is found in WO 01/58935, incorporated herein by reference.

Coupling to a Sugar Moiety

In order to achieve in vivo glycosylation of the polypeptide variant of the invention, the nucleotide sequence encoding the polypeptide variant must be inserted in a glycosylating, eukaryotic expression host. The expression host cell may be selected from fungal (filamentous fungal or yeast), insect or animal cells or from transgenic plant cells. In one embodiment the host cell is a mammalian cell, such as a CHO cell, a COS cell, a BHK cell or a HEK cell, e.g. a HEK 293 cell, or an insect cell, such as an SF9 cell, or a yeast cell, such as *S. cerevisiae* or *Pichia pastoris*, or any of the host cells mentioned hereinafter. Further information on in vivo glycosylation of FVII and FVIIa is found in WO 01/58935 and WO 03/093465, incorporated by reference.

Methods of Preparing a Polypeptide Variant of the Invention

The polypeptide variants of the present invention, optionally in glycosylated form, may be produced by any suitable method known in the art. Such methods include constructing a nucleotide sequence encoding the polypeptide variant and expressing the sequence in a suitable transformed or transfected host. Preferably, the host cell is a gamma-carboxylating host cell such as a mammalian cell. However, polypeptide variants of the invention may be produced, albeit less efficiently, by chemical synthesis or a combination of chemical synthesis or a combination of chemical synthesis and recombinant DNA technology.

A nucleotide sequence encoding a polypeptide variant of the invention may be constructed by isolating or synthesizing a nucleotide sequence encoding hFVII and then changing the nucleotide sequence so as to effect introduction (i.e. insertion or substitution) or removal (i.e. deletion or substitution) of the relevant amino acid residue(s).

The nucleotide sequence is conveniently modified by site-directed mutagenesis in accordance with conventional methods. Alternatively, the nucleotide sequence is prepared by chemical synthesis, e.g. by using an oligonucleotide synthesizer, wherein oligonucleotides are designed based on the amino acid sequence of the desired polypeptide variant, and preferably selecting those codons that are favored in the host cell in which the recombinant polypeptide variant will be produced. For example, several small oligonucleotides coding for portions of the desired polypeptide variant may be synthesized and assembled by PCR (polymerase chain reaction), ligation or ligation chain reaction (LCR) (Barany, *Proc Natl Acad Sci USA* 88:189-193, 1991). The individual oligonucleotides typically contain 5' or 3' overhangs for complementary assembly.

Once assembled (by synthesis, site-directed mutagenesis or another method), the nucleotide sequence encoding the polypeptide is inserted into a recombinant vector and operably linked to control sequences necessary for expression of the FVII in the desired transformed host cell.

Persons skilled will be capable of selecting suitable vectors, expression control sequences and hosts for expressing the polypeptide The recombinant vector may be an autonomously replicating vector, i.e. a vector, which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector in which the nucleotide sequence encoding the polypeptide variant of the invention is operably linked to additional segments required for transcription of the nucleotide sequence. The vector is typically derived from plasmid or viral DNA. A number of suitable expression vectors for expression in the host cells mentioned herein are commercially available or described in the literature. Detailed information on suitable vectors for expressing FVII may be found in WO 01/58935, incorporated by reference.

The term "control sequences" is defined herein to include all components which are necessary or advantageous for the expression of the polypeptide variant of the invention. Each control sequence may be native or foreign to the nucleic acid sequence encoding the polypeptide variant. Such control sequences include, but are not limited to, a leader sequence, polyadenylation sequence, propeptide sequence, promoter, enhancer or upstream activating sequence, signal peptide sequence, and transcription terminator. At a minimum, the control sequences include a promoter. A wide variety of expression control sequences may be used in the present invention, e.g. any of the control sequences disclosed in WO 01/58935, incorporated by reference.

The nucleotide sequence of the invention encoding a polypeptide variant, whether prepared by site-directed mutagenesis, synthesis, PCR or other methods, may optionally include a nucleotide sequence that encodes a signal peptide. The signal peptide is present when the polypeptide variant is to be secreted from the cells in which it is expressed. Such signal peptide, if present, should be one recognized by the cell chosen for expression of the polypeptide variant. The signal peptide may be homologous (i.e. normally associated with hFVII) or heterologous (i.e. originating from another source than hFVII) to the polypeptide or may be homologous or heterologous to the host cell, i.e. be a signal peptide normally expressed from the host cell or one which is not normally expressed from the host cell. For further information on suitable signal peptides, see WO 01/58935.

Any suitable host may be used to produce the polypeptide variant, including bacteria (although not particularly preferred), fungi (including yeasts), plant, insect, mammal, or other appropriate animal cells or cell lines, as well as transgenic animals or plants. Mammalian cells are preferred. Examples of bacterial host cells include gram-positive bacteria such as strains of *Bacillus*, e.g. *B. brevis* or *B. subtilis*, or *Streptomyces*, or gram-negative bacteria, such as strains of *E. coli*. Examples of suitable filamentous fungal host cells include strains of *Aspergillus*, e.g. *A. oryzae, A. niger*, or *A. nidulans, Fusarium* or *Trichodenna*. Examples of suitable yeast host cells include strains of *Saccharomyces*, e.g. *S. cerevisiae, Schizosaccharomyces, Kluyveromyces, Pichia*, such as *P. pastoris* or *P. methanolica, Hansenula*, such as *H. Polymorpha* or *Yarrowia*. Examples of suitable insect host cells include a *Lepidoptora* cell line, such as *Spodoptera frugiperda* (Sf9 or Sf21) or *Trichoplusioa ni* cells (High Five) (U.S. Pat. No. 5,077,214). Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)). Additional suitable cell lines are known in the art and available from public depositories such as the American Type Culture Collection, Rockville, Md. Also, mammalian cells, such as a CHO cell, may be modified to express sialyltransferase, e.g. 1,6-sialyltransferase, e.g. as described in U.S. Pat. No. 5,047,335, in order to provide improved glycosylation of the polypeptide variant.

Methods for introducing exogenous DNA into the above cell types, as well as other information regarding expression, production and purification of FVII variants, is found in WO 01/58935, incorporated herein by reference.

Pharmaceutical Composition of the Invention and its Use

In a further aspect, the present invention relates to a composition, in particular to a pharmaceutical composition, comprising a polypeptide variant of the invention and a pharmaceutically acceptable carrier or excipient.

The polypeptide variant or the pharmaceutical composition according to the invention may be used as a medicament.

Due to the high clotting efficiency, the polypeptide variant of the invention, or the pharmaceutical composition of the invention, is particular useful for the treatment of uncontrollable bleeding events in trauma patients, thrombocytopenic patients, patients in anticoagulant treatment, and cirrhosis patients with variceal bleeding, or other upper gastrointestinal bleedings, in patients undergoing orthotopic liver transplantation or liver resection (allowing for transfusion free surgery), or in hemophilia patients.

Trauma is defined as an injury to living tissue caused by an extrinsic agent. It is the $4^{th}$ leading cause of death in the US and places a large financial burden on the economy.

Trauma is classified as either blunt or penetrative. Blunt trauma results in internal compression, organ damage and internal haemorrhage whereas penetrative trauma (as the consequence of an agent penetrating the body and destroying tissue, vessels and organs) results in external haemorrhage.

Trauma may be caused by numerous events, e.g. traffic accidents, gunshot wounds, falls, machinery accidents, and stab wounds.

Cirrhosis of the liver may be caused by direct liver injury, including chronic alcoholism, chronic viral hepatitis (types B, C, and D), and autoimmune hepatitis as well as by indirect injury by way of bile duct damage, including primary biliary cirrhosis, primary sclerosing cholangitis and biliary atresia Less common causes of cirrhosis include direct liver injury from inherited disease such as cystic fibrosis, alpha-1-antitrypsin deficiency, hemochromatosis, Wilson's disease, galactosemia, and glycogen storage disease. Transplantation is the key intervention for treating late stage cirrhotic patients.

Thus, in a further aspect the present invention relates to a polypeptide variant of the invention for the manufacture of a medicament for the treatment of diseases or disorder wherein clot formation is desirable. A still further aspect of the present invention relates to a method for treating a mammal having a disease or disorder wherein clot formation is desirable, comprising administering to a mammal in need thereof an effective amount of the polypeptide variant or the pharmaceutical composition of the invention.

Examples of diseases/disorders wherein increased clot formation is desirable include, but is not limited to, hemorrhages, including brain hemorrhages, as well as patient with severe uncontrolled bleedings, such as trauma Further examples include patients undergoing transplantations, patients undergoing resection and patients with variceal bleedings. Another widespread disease/disorder in which it is contemplated that the polypeptides of the invention will be useful for increased clot formation is hemophilia, e.g. von Willebrand disease, hemophilia A, hemophilia B or hemophilia C.

The polypeptide variant of the invention is administered to patients in a therapeutically effective dose, normally one approximately paralleling that employed in therapy with rhFVII such as NOVOSEVEN®, or at lower dosage. By "therapeutically effective dose" herein is meant a dose that is sufficient to produce the desired effects in relation to the condition for which it is administered. The exact dose will depend on the circumstances, and will be ascertainable by one skilled in the art using known techniques. Normally, the dose should be capable of preventing or lessening the severity or spread of the condition or indication being treated. It will be apparent to those of skill in the art that an effective amount of a polypeptide variant or composition of the invention depends, inter alia, upon the disease, the dose, the administration schedule, whether the polypeptide variant or composition is administered alone or in conjunction with the other therapeutic agents, the plasma half-life of the compositions, and the general health of the patient.

The polypeptide variant of the invention is preferably administered in a composition including a pharmaceutically acceptable carrier or excipient. "Pharmaceutically acceptable" means a carrier or excipient that does not cause any untoward effects in patients to whom it is administered. Such pharmaceutically acceptable carriers and excipients are well known in the art (see, for example, Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

The polypeptide variants of the invention can be used "as is" and/or in a salt form thereof Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

The pharmaceutical composition of the invention may be administered alone or in conjunction with other therapeutic agents. These agents may be incorporated as part of the same pharmaceutical composition or may be administered separately from the polypeptide variant of the invention, either concurrently or in accordance with another treatment schedule. In addition, the polypeptide variant or pharmaceutical composition of the invention may be used as an adjuvant to other therapies.

A "patient" for the purposes of the present invention includes both humans and other mammals. Thus, the methods are applicable to both human therapy and veterinary applications.

The pharmaceutical composition comprising the polypeptide variant of the invention may be formulated in a variety of forms, e.g. as a liquid, gel, lyophilized, or as a compressed solid. The preferred form will depend upon the particular indication being treated and will be apparent to one skilled in the art.

In particular, the pharmaceutical composition comprising the polypeptide variant of the invention may be formulated in lyophilized or stable soluble form. The polypeptide variant may be lyophilised by a variety of procedures known in the art. The polypeptide variant may be in a stable soluble form by the removal or shielding of proteolytic degradation sites as described herein. The advantage of obtaining a stable soluble preparation lies in easier handling for the patient and, in the case of emergencies, quicker action, which potentially can become life saving. The preferred form will depend upon the particular indication being treated and will be apparent to one of skill in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner. The formulations can be administered continuously by infusion, although bolus injection is acceptable, using techniques well known in the art, such as pumps or implantation. In some instances the formulations may be directly applied as a solution or spray.

Parenterals

A preferred example of a pharmaceutical composition is a solution, in particular an aqueous solution, designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide variant having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic surfactants or detergents, antioxidants and/or other miscellaneous additives.

Detailed information on parental formulations suitable for administration of FVII variants, as well as sustained release preparations, is found in WO 01/58935 and WO 03/093465, incorporated herein by reference.

The invention is further described in the following non-limiting examples.

MATERIALS AND METHODS

Active Site Region

The active site region is defined as any residues having at least one atom within 10 Å of any atom in the catalytic triad (residues H193, D242, S344).

Measurement of Reduced Sensitivity to Proteolytic Degradation

Proteolytic degradation can be measured using the assay described in U.S. Pat. No. 5,580,560, Example 5, where proteolysis is autoproteolysis.

Furthermore, reduced proteolysis can be tested in an in vivo model using radiolabelled samples and comparing proteolysis of rhFVIIa and the polypeptide variant of the invention by withdrawing blood samples and subjecting these to SDS-PAGE and autoradiography.

Irrespectively of the assay used for determining proteolytic degradation, "reduced proteolytic degradation" is intended to mean a measurable reduction in cleavage compared to that obtained by rhFVIIa as measured by gel scanning of Coomassie stained SDS-PAGE gels, HPLC or as measured by conserved catalytic activity in comparison to wild type using the tissue factor independent activity assay described below.

Determination of the Molecular Weight of Polypeptide Variants

The molecular weight of polypeptide variants is determined by either SDS-PAGE, gel filtration, Western Blots, matrix assisted laser desorption mass spectrometry or equilibrium centrifugation, e.g. SDS-PAGE according to Laemmli, U. K., *Nature* Vol 227 (1970), pp. 680-85.

Determination of TFPI Inhibition

FVII inhibition by TFPI can be monitored in the amidolytic assay described in Chang et al. *Biochemistry* 1999, 38: 10940-10948.

Determination of TFPI Affinity

The capacity of variants to bind to TFPI is evaluated using one or more of the three BIAcore® assays described in Dickinson et al. *Proc. Natl. Acad. Sci. USA* 1996, 93: 14379-14384; Roberge et al. *Biochemistry* 2001, 40: 9522-9531; and Ruf et al. *Biochemistry* 1999, 38(7): 1957-1966.

TF-Independent Factor X Activation Assay

This assay has been described in detail on page 39826 in Nelsestuen et al., *J Biol Chem*, 2001; 276:39825-39831.

Briefly, the molecule to be assayed (either hFVIIa, rhFVIIa or the polypeptide variant of the invention in its activated form) is mixed with a source of phospholipid (preferably phosphatidylcholine and phosphatidylserine in a ratio of 8:2) and relipidated Factor X in Tris buffer containing BSA. After a specified incubation time the reaction is stopped by addition of excess EDTA. The concentration of factor Xa is then measured from absorbance change at 405 nm after addition of a chromogenic substrate (S-2222, Chromogenix). After correction from background the tissue factor independent activity of rhFVIIa ($a_{wt}$) is determined as the absorbance change after 10 minutes and the tissue factor independent activity of the polypeptide variant of the invention ($a_{variant}$) is also determined as the absorbance change after 10 minutes. The ratio between the activity of the polypeptide variant, in its activated form, and the activity of rhFVIIa is defined as $a_{variant}/a_{wt}$.

Clotting Assay

The clotting activity of the FVIIa and variants thereof were measured in one-stage assays and the clotting times were recorded on a Thrombotrack IV coagulometer (Medinor). Factor VII-depleted human plasma (American Diagnostica) was reconstituted and equilibrated at room temperature for 15-20 minutes. 50 microliters of plasma was then transferred to the coagulometer cups.

FVIIa and variants thereof were diluted in Glyoxaline Buffer (5.7 mM barbiturate, 4.3 mM sodium citrate, 117 mM NaCl, 1 mg/ml BSA, pH 7.35). The samples were added to the cup in 50 ul and incubated at 37° C. for 2 minutes.

Technoplastin His (Medinor) was reconstituted with water and $CaCl_2$ was added to a final concentration of 4.5 mM. The mixture was equilibrated at 37° C. for 15-20 min. The reaction was initiated by adding 100 µl Technoplastin His.

To measure the clotting activity in the absence of TF the same assay was used without addition of Technoplastin His. Data was analyzed using PRISM software.

Whole Blood Assay

The clotting activity of FVIIa and variants thereof were measured in one-stage assays and the clotting times were recorded on a Thrombotrack IV coagulometer (Medinor). 100 µl of FVIIa or variants thereof were diluted in a buffer containing 10 mM glycylglycine, 50 mM NaCl, 37.5 mM $CaCl_2$, pH 7.35 and transferred to the reaction cup. The clotting reaction was initiated by addition of 50 µl blood containing 10% 0.13 M tri-sodium citrate as anticoagulant. Data was analyzed using Excel or PRISM software.

Amidolytic Assay

The ability of the variants to cleave small peptide substrates can be measured using the chromogenic substrate S-2288 (D-Ile-Pro-Arg-p-nitroanilide). FVIIa is diluted to about 10-90 nM in assay buffer (50 mM Na-Hepes pH 7.5, 150 mM NaCl, 5 mM CaCl$_2$, 0.1% BSA, 1 U/ml Heparin). Furthermore, soluble TF (sTF) is diluted to 50-450 nM in assay buffer. 120 µl of assay buffer is mixed with 20 µl of the FVIIa sample and 20 µl sTF. After 5 min incubation at room temperature with gentle shaking, followed by 10 min incubation at 37° C., the reaction is started by addition of the S-2288 substrate to 1 mM and the absorption at 405 nm is determined at several time points.

ELISA Assay

FVII/FVIIa (or variant) concentrations are determined by ELISA. Wells of a microtiter plate are coated with an antibody directed against the protease domain using a solution of 2 µg/ml in PBS (100 µl per well). After overnight coating at R.T. (room temperature), the wells are washed 4 times with THT buffer (100 mM NaCL, 50 mM Tris-HCl pH 7.2 0.05% Tween-20). Subsequently, 200 µl of 1% Casein (diluted from 2.5% stock using 100 mM NaCl, 50 mM Tris-HCl pH 7.2) is added per well for blocking. After 1 hr incubation at R.T., the wells are emptied, and 100 µl of sample (optionally diluted in dilution buffer (THT+0.1% Casein)) is added. After another incubation at 1 hr at room temperature, the wells are washed 4 times with THT buffer, and 100 µl of a biotin-labelled antibody directed against the EGF-like domain (1 µg/ml) is added. After another 1 hr incubation at R.T., followed by 4 more washes with THT buffer, 100 µl of streptavidin-horse radish peroxidase (DAKO A/S, Glustrup Denmark, diluted 1/10000) is added. After another 1 hr incubation at R.T., followed by 4 more washes with THT buffer, 100 µl of TMB (3,3',5,5'-tetramethylbenzidine, Kem-enTech A/S, Denmark) is added. After 30 min incubation at R.T. in the dark, 100 µl of 1 M H$_2$SO$_4$ is added and OD$_{450nm}$ is determined. A standard curve is prepared using rhFVIIa (NOVOSEVEN®).

Alternatively, FVII/FVIIa or variants may be quantified through the Gla domain rather than through the protease domain. In this ELISA set-up, wells are coated overnight with an antibody directed against the EGF-like domain and for detection, a calcium-dependent biotin-labelled monoclonal anti-Gla domain antibody is used (2 µg/ml, 100 µl per well). In this set-up, 5 mM CaCl$_2$ is added to the THT and dilution buffers.

EXAMPLES

Example 1

The X-ray structure of hFVIIa in complex with soluble tissue factor by Banner et al., *J Mol Biol*, 1996; 285:2089 is used for this example. It is noted that the numbering of residues in the reference does not follow the sequence. Here, we have used the sequential numbering according to SEQ ID NO:2. The gamma-carboxy glutamic acids at positions 6, 7, 14, 16, 19, 20, 25, 26, 29 and 35 are all here named Glu (three letter abbreviation) or E (one letter abbreviation). Residues 143-152 are not present in the structure. For further information on the calculations in this example, see WO 01/58935.

Surface Exposure

Performing fractional ASA calculations resulted in the following residues being determined to have more than 25% of their side chain exposed to the surface: A1, N2, A3, F4, L5, E6, E7, L8, R9, P10, S12, L13, E14, E16, K18, E19, E20, Q21, S23, F24, E25, E26, R28, E29, F31, K32, D33, A34, E35, R36, K38, L39, W41, I42, S43, S45, G47, D48, Q49, A51, S52, S53, Q56, G58, S60, K62, D63, Q64, L65, Q66, S67, I69, F71, L73, P74, A75, E77, G78, R79, E82, T83, H84, K85, D86, D87, Q88, L89, I90, V92, N93, E94, G97, E99, S103, D104, H105, T106, G107, T108, K109, S111, R113, E116, G117, S119, L120, L121, A122, D123, G124, V125, S126, T128, P129, T130, V131, E132, I140, L141, E142, K143, R144, N145, A146, S147, K148, P149, Q150, G151, R152, G155, K157, V158, P160, K161, E163, L171, N173, G174, A175, N184, T185, I186, H193, K197, K199, N200, R202, N203, I205, S214, E215, H216, D217, G218, D219, S222, R224, S232, T233, V235, P236, G237, T238, T239, N240, H249, Q250, P251, V253, T255, D256, E265, R266, T267, E270, R271, F275, V276, R277, F278, L280, L287, L288, D289, R290, G291, A292, T293, L295, E296, N301, M306, T307, Q308, D309, L311, Q312, Q313, R315, K316, V317, G318, D319, S320, P321, N322, T324, E325, Y326, Y332, S333, D334, S336, K337, K341, G342, H351, R353, G354, Q366, G367, T370, V371, G372, R379, E385, Q388, K389, R392, S393, E394, P395, R396, P397, G398, V399, L400, L401, R402, P404 and P406.

The following residues were determined to have more than 50% of their side chain exposed to the surface: A1, A3, F4, L5, E6, E7, L8, R9, P10, E14, E16, K18, E19, E20, Q21, S23, E25, E26, E29, K32, A34, E35, R36, K38, L39, I42, S43, G47, D48, A51, S52, S53, Q56, G58, S60, K62, L65, Q66, S67, I69, F71, L73, P74, A75, E77, G78, R79, E82, H84, K85, D86, D87, Q88, L89, I90, V92, N93, E94, G97, T106, G107, T108, K109, S111, E116, S119, L121, A122, D123, G124, V131, E132, L141, E142, K143, R144, N145, A146, S147, K148, P149, Q150, G151, R152, G155, K157, P160, N173, G174, A175, K197, K199, N200, R202, S214, E215, H216, G218, R224, V235, P236, G237, T238, H249, Q250, V253, D256, T267, F275, R277, P278, L288, D289, R290, G291, A292, T293, L295, N301, M306, Q308, D309, L311, Q312, Q313, R315, K316, G318, D319, N322, E325, D334, K341, G354, G367, V371, E385, K389, R392, E394, R396, P397, G398, R402, P404 and P406.

Tissue Factor Binding Site

It was determined using ASA calculations that the following residues in hFVII change their ASA in the complex. These residues were defined as constituting the tissue factor binding site: L13, K18, F31, E35, R36, L39, F40, I42, S43, S60, K62, D63, Q64, L65, I69, C70, F71, C72, L73, P74, F76, E77, G78, R79, E82, K85, Q88, I90, V92, N93, E94, R271, A274, F275, V276, R277, F278, R304, L305, M306, T307, Q308, D309, Q312, Q313, E325 and R379.

Active Site Region

The active site region is defined as any residue having at least one atom within a distance of 10 Å from any atom in the catalytic triad (residues H193, D242, S344): I153, Q167, V168, L169, L170, L171, Q176, L177, C178, G179, G180, T181, V188, V189, S190, A191, A192, H193, C194, F195, D196, K197, I198, W201, V228, I229, I230, P231, S232, T233, Y234, V235, P236, G237, T238, T239, N240, H241, D242, I243, A244, L245, L246, V281, S282, G283, W284, G285, Q286, T293, T324, E325, Y326, M327, F328, D338, S339, C340, K341, G342, D343, S344, G345, G346, P347, H348, L358, T359, G360, I361, V362, S363, W364, G365, C368, V376, Y377, T378, R379, V380, Q382, Y383, W386, L387, L400 and F405.

The Ridge of the Active Site Binding Cleft

The ridge of the active site binding cleft region was defined by visual inspection of the FVIIa structure 1FAK.pdb as: N173, A175, K199, N200, N203, D289, R290, G291, A292, P321 and T370.

Example 2

Design of an Expression Cassette for Expression of hFVII in Mammalian Cells The DNA sequence shown in SEQ ID NO:1, encompassing the short form of the full length cDNA encoding hFVII with its native short signal peptide (Hagen et al., 1986. *Proc Natl Acad Sci USA* 83:2412), was synthesized in order to facilitate high expression in mammalian cells. First the ATG start codon context was modified according to the Kozak consensus sequence (Kozak, M. *J Mol Biol* 1987 Aug. 20; 196(4): 947-50), so that there is a perfect match to the consensus sequence upstream of the ATG start codon. Secondly the open reading frame of the native cDNA was modified by making a bias in the codon usage towards the codons frequently used in highly expressed human genes. Further, two translational stop codons were inserted at the end of the open reading frame in order to facilitate efficient translational stop. The fully synthetic and expression optimized hFVII gene was assembled from 70-mer DNA oligonucleotides and finally amplified using end primers inserting BamHI and HindIII sites at the 5' and 3' ends respectively using standard PCR techniques, which resulted in the following sequence (SEQ ID NO:3):

```
ggatccgccaccatggtcagccaggccctccgcctcctgtgcctgctcc tggggctgcagggctgcctggctgccgtcttcgtcacccaggaggaagcc catggcgtcctgcatcgccggcgccgggccaatgcctttctggaagagct ccgccctggctccctggaacgcgaatgcaaagaggaacagtgcagctttg aggaagcccgggagattttcaaagacgctgagcggaccaaactgttttgg attagctatagcgatggcgatcagtgcgcctccagcccttgccagaacgg gggctcctgcaaagaccagctgcagagctatatctgcttctgcctgcctg cctttgaggggcgcaattgcgaaacccataaggatgaccagctgatttgc gtcaacgaaaacggggctgcgagcagtactgcagcgatcacacgggcac gaagcggagctgccgctgccacgaaggctatagcctcctggctgacgggg tgtcctgcacgcccacggtggaataccttgcgggaagattcccattcta gaaaagcggaacgctagcaaacccagggccggatcgtcggcgggaaggt ctgccctaagggggagtgcccctggcaggtcctgctcctggtcaacgggg cccagctgtgcggcgggaccctcatcaataccatttgggtcgtgtccgcc gctcactgcttcgataagattaagaattggcggaacctcatcgctgtgct cggcgaacacgatctgtccgagcatgacggggacgaacagtcccgccggg tggctcaggtcatcattccctccacctatgtgcctggcacgaccaatcac gatatcgctctgctccgcctccaccagcccgtcgtgctcaccgatcacgt cgtgcctctgtgcctgcctgagcggaccctttagcgaacgcacgctggctt tcgtccgctttagcctcgtgtccggctggggccagctgctcgaccggggc gctaccgctctcgagctgatggtgctcaacgtccccggctgatgaccca
```

```
ggactgcctgcagcagtcccgcaaagtgggggactccccaatatcacgg agtatatgttttgcgctggctatagcgatggctccaaggatagctgcaag ggggactccggcgggcccatgccacgcactatcgcgggacctggtacct caccgggatcgtcagctggggccagggctgcgccacggtggggcactttg gcgtctacacgcgcgtcagccagtacattgagtggctgcagaagctcatg cggagcgaacccggcccggggtgctcctgcgggcccctttcccttgata aaagctt
```

A vector for the cloning of the generated PCR product encompassing the expression cassette for hFVII was prepared by cloning the intron from pCINeo (Promega). The synthetic intron from pCI-Neo was amplified using standard PCR conditions and the primers:

```
CBProFpr174:                              (SEQ ID NO: 4)
5'-AGCTGGCTAGCCACTGGGCAGGTAAGTATCA-3'
and CBProFpr175:                              (SEQ ID NO: 5)
5'-TGGCGGGATCCTTAAGAGCTGTAATTGAACT-3'
``` resulting in a 332 bp PCR fragment. The fragment was cut with NheI and BamHI before cloning into pCDNA3.1/HygR (obtained from Invitrogen) resulting in PF#34.

The expression cassette for hFVII was cloned between the BamHI and HindIII sites of PF#341, resulting in plasmid PF#226.

Example 3

Construction of Expression Vectors Encoding Polypeptide Variants of the Invention Sequence overhang extension (SOE) PCR was used for generating constructs having variant FVII open reading frames with substituted codons. In the SOE-PCR both the N-terminal part and the C-terminal part of the FVII open reading frame was first amplified in individual primary PCRs.

In order to change the codon for D196 to the codon for N196 the following primers were used pairwise for the primary PCRs:

```
                                          (SEQ ID NO: 6)
CB499: 5'-CCCATTCTAGAAAAGCGGAACGCCAGCAAACCCAGGG-3'
and (SEQ ID NO: 7)
CB562: 5'-CCAATTCTTAATCTTGTTGAAGCAGTGAGCGGCG-3',
and (SEQ ID NO: 8)
CB256: 5'-CTCCGTGATATTGGGGGAGTC-3'
and (SEQ ID NO: 9)
CB561: 5'-CGCCGCTCACTGCTTCAACAAGATTAAGAATTGG-3'.
```

The primary PCR products were then combined and the terminal primers (CB499 and CB256) were added, allowing for the secondary full-length product encoding the mutated fragment of the desired D196N variant to be made. This PCR product was restricted with XbaI and XhoI and used to substitute the equivalent fragment of the FVII coding region of expression vector PF226 resulting in the expression vector pB0014 encoding the D196N variant.

With the exception of the constructs for position 341 variants, the constructs were made in the same way as for D196N. Constructs for position 341 variants were made using the end primers

```
CB220: 5'-CGCTCTCGAGCTGATGGTGCTC-3'   (SEQ ID NO: 10)
and

CB362: 5'-CAAACAACAGATGGCTGGCAAC-3'   (SEQ ID NO: 11)
``` allowing for directional cloning between XhoI and HindIII. The central primer used in the SOE-PCR reactions for the substitution variants were:

```
D196K
CB563:
CGCCGCTCACTGCTTCAAGAAGATTAAGAATTGG (SEQ ID NO: 12)

CB564:
CCAATTCTTAATCTTCTTGAAGCAGTGAGCGGCG (SEQ ID NO: 13)

G237L
CB565:
CTCCACCTATGTGCCTCTGACGACCAATCACGA  (SEQ ID NO: 14)

CB566:
TCGTGATTGGTCGTCAGAGGCACATAGGTGGAG  (SEQ ID NO: 15)

K341Q
CB569:
CCAAGGATGCCAGGGGGACTCCGGCGGGC      (SEQ ID NO: 16)

CB570:
GCCCGCCGGAGTCCCCCTGGCAGCTATCCTTGG  (SEQ ID NO: 17)
```

For the insertion variant the central primers were:

```
G237GAA
CB597:
ACCTATGTGCCTGGCGCTGCCACGAC-        (SEQ ID NO: 18)
CAATCACGAT

CB598:
ATCGTGATTGGTCGTGGCAGCGCCAG-        (SEQ ID NO: 19)
GCACATAGGT
```

Example 4

Expression of FVII or FVII Variants in CHO K1 Cells

The cell line CHO K1 (ATCC # CCL-61) is seeded at 50% confluence in T-25 flasks using MEMα, 10% FCS (Gibco/BRL Cat # 10091), P/S and 5 µg/ml phylloquinone and allowed to grow until confluent. The confluent mono cell layer is transfected with 5 µg of the relevant plasmid described above using the Lipofectamine 2000 transfection agent (Life Technologies) according to the manufacturer's instructions. Twenty four hours post transfection a sample is drawn and quantified using e.g. an ELISA recognizing the EGF1 domain of hFVII. At this time point relevant selection (e.g. Hygromycin B) may be applied to the cells for the purpose of generating a pool of stable transfectants. When using CHO K1 cells and the Hygromycin B resistance gene as a selectable marker on the plasmid, this is usually achieved within one week.

Example 5

Generation of CHO-K1 Cells Stably Expressing Polypeptide Variants

A vial of CHO-K1 transfectant pool is thawed and the cells seeded in a 175 $cm^2$ tissue flask containing 25 ml of MEMα, 10% FCS, phylloquinone (5 µg/ml), 100 U/l penicillin, 100 µg/l streptomycin and grown for 24 hours. The cells are harvested, diluted and plated in 96 well microtiter plates at a cell density of ½-1 cell/well. After a week of growth, colonies of 20-100 cells are present in the wells and those wells containing only one colony are labelled. After a further two weeks, the media in all wells containing only one colony is substituted with 200 µl fresh medium. After 24 hours, a medium sample is withdrawn and analyzed by e.g. ELISA. High producing clones are selected and used to produce FVII or variant on large scale.

Example 6

Purification of Polypeptide Variants and Subsequent Activation

FVII and FVII variants are purified as follows: The procedure is performed at 4° C. The harvested culture media from large-scale production is ultrafiltered using a Millipore TFF system with 30 KDa cut-off Pellicon membranes. After concentration of the medium, citrate is added to 5 mM and the pH is adjusted to 8.6. If necessary, the conductivity is lowered to below 10 mS/cm. Subsequently, the sample is applied to a Q-sepharose FF column, equilibrated with 50 mM NaCl, 10 mM Tris pH 8.6. After washing the column with 100 mM NaCl, 10 mM Tris pH 8.6, followed by 150 mM NaCl, 10 mM Tris pH 8.6, FVII is eluted using 10 mM Tris, 25 mM NaCl, 35 mM $CaCl_2$, pH 8.6.

For the second chromatographic step, an affinity column is prepared by coupling of a monoclonal Calcium-dependent antiGla-domain antibody to CNBr-activated Sepharose FF. About 5.5 mg antibody is coupled per ml resin. The column is equilibrated with 10 mM Tris, 100 mM NaCl, 35 mM $CaCl_2$, pH 7.5. NaCl is added to the sample to a concentration of 100 mM NaCl and the pH is adjusted to 7.4-7.6. After O/N application of the sample, the column is washed with 100 mM NaCl, 35 mM $CaCl_2$, 10 mM Tris pH 7.5, and the FVII protein is eluted with 100 mM NaCl, 50 mM citrate, 75 mM Tris pH 7.5.

For the third chromatographic, the conductivity of the sample is lowered to below 10 mS/cm, if necessary, and the pH is adjusted to 8.6. The sample is then applied to a Q-sepharose column (equilibrated with 50 mM NaCl, 10 mM Tris pH 8.6) at a density around 3-5 mg protein per ml gel to obtain efficient activation. After application, the column is washed with 50 mM NaCl, 10 mM Tris pH 8.6 for about 4 hours with a flow of 3-4 column volumes (cv) per hour. The FVII protein is eluted using a gradient of 0-100% of 500 mM NaCl, 10 mM Tris pH 8.6 over 40 cv. FVII containing fractions are pooled.

For the final chromatographic step, the conductivity is lowered to below 10 mS/cm. Subsequently, the sample is applied to a Q-sepharose column (equilibrated with 140 mM NaCl, 10 mM glycylglycine pH 8.6) at a concentration of 3-5 mg protein per ml gel. The column is then washed with 140 mM NaCl, 10 mM glycylglycine pH 8.6 and FVII is eluted with 140 mM NaCl, 15 mM CaCl$_2$, 10 mM glycylglycine pH 8.6. The eluate is diluted to 10 mM CaCl$_2$ and the pH is adjusted 6.8-7.2. Finally, Tween-80 is added to 0.01% and the pH is adjusted to 5.5 for storage at −80° C.

Example 7

Experimental Results

Subjecting the variants of the invention to the "Whole Blood Assay" revealed that the variants exhibit a significantly increased clotting activity (reduced clotting time) as compared to rhFVIIa. The experimental results are compiled in Table 1 below. The results are in addition illustrated in the appended FIG. 1, which shows the clotting time vs. concentration for the G237GAA variant versus rhFVIIa.

TABLE 1

| Variant | Clotting time (Whole Blood Assay) $t_{variant}/t_{wt}$ |
| --- | --- |
| rhFVIIa (reference) | 1 |
| D196K | 0.4 |
| D196N | 0.4 |
| K341Q | 0.4 |
| G237L | 0.3 |
| G237GAA | 0.3 |

The invention claimed is:

1. A variant of Factor VII (FVII) or Factor VIIa (FVIIa), wherein said variant comprises 1-15 amino acid modifications within human Factor VII (hFVII) or human Factor VIIa (hFVIIa) comprising SEQ ID NO:2, wherein at least one amino acid modification comprises a substitution D196K in SEQ ID NO:2.

2. The variant of claim 1, wherein said variant further comprises a modification in position 237 as compared to hFVII or hFVIIa (SEQ ID NO:2).

3. The variant of claim 2, wherein said modification is a substitution.

4. The variant of claim 3, wherein said substitution is G237L.

5. The variant of claim 2, wherein said modification is an insertion.

6. The variant of claim 5, wherein said insertion at amino acid residue 237 is selected from the group consisting of G237GXX, G237GXXX and G237GXXXX, wherein X is any amino acid residue.

7. The variant of claim 6, wherein X is selected from the group consisting of Ala, Val, Leu, Ile, Gly, Ser and Thr.

8. The variant of claim 7, wherein X is Ala.

9. The variant of claim 8, wherein said insertion is G237GAA.

10. The variant of claim 1, wherein said variant further comprises a modification in position 341 as compared to hFVII or hFVIIa comprising SEQ ID NO:2.

11. The variant of claim 10, wherein said modification is a substitution.

12. The variant of claim 11, wherein said substitution is K341Q.

13. The variant of claim 1, wherein said variant is in its activated form.

14. A composition comprising a variant as defined in claim 1 and at least one pharmaceutically acceptable carrier or excipient.

15. A method for treating a mammal having a disease or disorder wherein clot formation is desirable, comprising administering to said mammal in need thereof an effective amount of the variant of claim 1.

16. The method of claim 15, wherein said disease or disorder is selected from the group consisting of hemorrhages, including brain hemorrhages, sever uncontrolled bleedings, bleedings in patients undergoing transplantations or resection, variceal bleedings, and hemophilia.

17. The method of claim 16, wherein said disease or disorder is trauma.

18. The method of claim 16, wherein said disease or disorder is hemophilia.

* * * * *